(12) United States Patent
Kane et al.

(10) Patent No.: US 7,193,070 B2
(45) Date of Patent: Mar. 20, 2007

(54) ISOLATED DNA MOLECULES ENCODING HUMANIZED CALCITONIN GENE-RELATED PEPTIDE RECEPTOR, RELATED NON-HUMAN TRANSGENIC ANIMALS AND ASSAY METHODS

(75) Inventors: Stefanie A. Kane, Schwenksville, PA (US); Christopher A. Salvatore, Philadelphia, PA (US); John J. Mallee, Collegeville, PA (US); Kenneth S. Koblan, Carversville, PA (US); Kevin R. Oliver, Huntingdon (GB)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 10/490,594

(22) PCT Filed: Sep. 26, 2002

(86) PCT No.: PCT/US02/30501

§ 371 (c)(1),
(2), (4) Date: Mar. 23, 2004

(87) PCT Pub. No.: WO03/027252

PCT Pub. Date: Apr. 3, 2003

(65) Prior Publication Data

US 2004/0197859 A1    Oct. 7, 2004

Related U.S. Application Data

(60) Provisional application No. 60/325,295, filed on Sep. 27, 2001.

(51) Int. Cl.
*C07K 1/00* (2006.01)
*C07K 14/00* (2006.01)
*C07K 17/00* (2006.01)
*C12N 15/00* (2006.01)
*C07H 21/02* (2006.01)
*C07H 21/04* (2006.01)

(52) U.S. Cl. .................. 536/23.1; 435/320.1; 435/325; 435/455; 530/350

(58) Field of Classification Search ............... 536/23.1; 435/320.1; 530/350
See application file for complete search history.

(56) References Cited

OTHER PUBLICATIONS

Doods et al. (2000, British Journal of Pharmacology, 129: 420-423).*
Salvatore, NCBI sequence submission, Sep. 26, 2001, gi No. 20257379.*
McLatchie et al. 1998, Nature, 393: 333-339.*
Fischer et al., Biochemical Society Transactions, 30: 455-460.*
Fitzsimmons et al., JBC, 27: 14313-14320.*
Conner, et al., 2002, Biochemical Society Transactions, 4: 451-455.*
Steiner et al., 2002, Biochemistry, 41: 11398-11404.*
Husmann et al. 'Mouse receptor-activity-modifying proteins 1,2- and -3: amino acid sequence, expression and function', Molecular and Cellular Endocrinology, 162 (2000) 35-43.
Nagae et al. 'Rat Receptor-Activity-Modifying Proteins (RAMPs) for Adrenomedullin/CGRP Receptor: Cloning and Upregulation on Obstructive Nephropathy', Biochemical and Biophysical Research Communications, 270, 89-93 (2000).
Chakravarty et al. 'CGRP and adrenomedullin binding correlates with transcript levels for Calcitonin Receptor-like Receptor (CRLR) and Receptor Activity Modifying Proteins (RAMPs) in rat tissues', British Journal of Pharmacology (2000) 130, 189-195.
McLatchie et al. 'RAMPs regulate the transport and ligand specificity fo the calcitonon-receptor-like receptor', Nature, vol. 393, p. 333-33928 May 1998.
Balkan et al. 'Testes Exhibit Elevated Expression of Calcitonin Gene Related Peptide Receptor Component Protein', Endo, 1999, vol. 140, No. 3 pp. 1459-1469.
Aiyar et al. 'A cDNA Encoding the Calcitonin Gene-related Peptide Type 1 Receptor', The Journal of Biological Chemistry, vol. 271, No. 19, Issueof May 10, pp. 11325-11329, 1996.
EMBL/GenBank/DDBJ databases, Submitted Aug. 30, 1999 (Q95574/AAG09434).
Luebke et al. 'Identification of a protein that confers calcitonin gene-related peptide responsiveness to oocytes by using a cystic fibrosis transmembrane conductance regulatory assay', Proc. Natl. Acad. Sci USA, vol. 93, pp. 3455-3460 Apr. 1996.
Doods et al., 'Pharmacological profile of BIBN4096BS, the first selective small molecule CGRP antagonist', British Journal of Pharmacology, vol. 129, pp. 420-423 (2000).

* cited by examiner

*Primary Examiner*—Anne M. Wehbe'
*Assistant Examiner*—Joanne Hama
(74) *Attorney, Agent, or Firm*—Henry P. Wu; Jack L. Tribble; Michael D. Yablonsky

(57) ABSTRACT

Disclosed herein are isolated nucleic acid molecules encoding a humanized version of a calcitonin gene-related peptide (CGRP) receptor, which comprises the G-protein coupled receptor calcitonin-receptor-like receptor (CRLR) and the receptor-activity-modifying protein 1 (RAMP1). The humanized CGRP receptors of the present invention attain pharmacological profiles similar to the wild type human receptor via modifications to the respective mammalian RAMP1 nucleotide sequence, specifically at amino acid 74. Also described are related recombinant vectors, recombinant hosts and associated methods for generating such humanized CGRP receptors. Also presented are non-human transgenic animals which express humanized RAMP1. Such animals have been engineered to provide for a CGRP pharmacological profile similar to human CGRP.

8 Claims, 5 Drawing Sheets

Figure 1: Alignment of human, rat and mouse RAMP1 protein sequences.

```
Human: 1    MARALCRLPRRGLWLLLAHHLFMTTACQEANYGALLRELCLTQFQVDMEAVGETLWCDWG 60
Rat  : 1    MAPGLRGLPRRGLWLLLAHHLFMVTACRDPDYGTLIQELCLSRFKEDMETIGKTLWCDWG 60
Mouse: 1    MAPGLRGLPRCGLWLLLAHHLFMVTACRDPDYGTLIQELCLSRFKENMETIGKTLWCDWG 60

74
Human: 61   RTIRSYRELADCTWHMAEKLGCFWPNAEVDRFFLAVHGRYFRSCPISGRAVRDPPGSILY 120
Rat  : 61   KTIGSYGELTHCTKLVANKIGCFWPNPEVDKFFIAVHHRYFSKCPVSGRALRDPPNSILC 120
Mouse: 61   KTIQSYGELTYCTKHVAHTIGCFWPNPEVDRFFIAVHHRYFSKCPISGRALRDPPNSILC 120

```
human    YRELADCTWHMAEKLGCFWPNAEVDRFFLAVHGRYFRSCPISGRAVR  (within SEQ ID NO: 16)
marmoset YRDLADCTWQVTEKLGCFWPNAEVDRFFLAVHGHYFRSCPVSGRAVR  (SEQ ID NO: 35)
rat      YGELTHCIKLVANKIGCFWPNPEVDKFFIAVHHRYFSKCPVSGRALR  (within SEQ ID NO: 18)
mouse    YGELTYCTKHVAHTIGCFWPNPEVDRFFIAVHHRYFSKCPISGRALR  (within SEQ ID NO: 20)
pig      YKDLSDCTRLVAQRLDCFWPNAAVDKFFLGVHQQYFRNCPVSGRALQ  (within SEQ ID NO: 24)
```

FIGURE 4

ISOLATED DNA MOLECULES ENCODING HUMANIZED CALCITONIN GENE-RELATED PEPTIDE RECEPTOR, RELATED NON-HUMAN TRANSGENIC ANIMALS AND ASSAY METHODS

CROSS-REFERENCE TO RELATED APPLICATIONS

This application claims benefit, under 35 U.S.C. §119(e), to U.S. provisional application 60/325,295 filed Sep. 27, 2001.

STATEMENT REGARDING FEDERALLY-SPONSORED R&D

Not Applicable

REFERENCE TO MICROFICHE APPENDIX

Not applicable.

FIELD OF THE INVENTION

The present invention relates in part to isolated nucleic acid molecules (polynucleotides) which encode a humanized version of a calcitonin gene-related peptide (CGRP) receptor, which comprises the G-protein coupled receptor calcitonin-receptor-like receptor (CRLR) and the receptor-activity-modifying protein 1 (RAMP1). The humanized CGRP receptors of the present invention attain pharmacological profiles similar to the wild type human receptor via modifications to the respective mammalian RAMP1 nucleotide sequence. The present invention also relates to recombinant vectors and recombinant hosts which contain a DNA fragment encoding a humanized version of a CGRP receptor, substantially purified forms of associated humanized version of a CGRP receptor, recombinant membrane fractions comprising these proteins, associated mutant proteins, and methods associated with identifying compounds which specifically modulated human CGRP receptor activity utilizing the humanized version of RAMP1 in various assays. The present invention also relates to cells and non-human transgenic animals wherein the endogenous gene encoding RAMP1 has been engineered to provide for a CGRP receptor pharmacological profile similar to the human CGRP receptor. Therefore, the transgenic animals of the present invention will provide for a phenotype whereby their pharmacological profile in regard to modulators of the CGRP receptor will mimic the human form of the receptor, not the form of the CGRP receptor endogenous to the transgenic animal. The present invention also relates to methods of screening for CGRP modulators which comprises utilizing a humanized version of the CGRP receptor to selectively identify modulators of human CGRP. Such CGRP receptor modulators will potentially be useful in the treatment of various disorders, including but not limited to migraine headaches, pain indications, menopausal hot flashes, migraine prophylaxis, chronic tension type headache, cluster headache, neurogenic or chronic inflammation, gastrointestinal disorders, type 2 diabetes and cardiovascular disorders.

BACKGROUND OF THE INVENTION

Calcitonin gene-related protein (CGRP) is a 37-amino acid neuropeptide that is expressed in a variety of cell types in both the central and peripheral nervous systems. In many tissues, CGRP-containing fibers are closely associated with blood vessels. Among the various physiological functions reported for CGRP, the most pronounced is vasodilation. CGRP is the most powerful of the vasodilator transmitters and its vasoactive effects have been demonstrated in a variety of blood vessels, including those in the cerebral, coronary, and mesenteric vasculature.

Mounting evidence suggests that CGRP is involved in the pathophysiology of migraine headache. Migraine is thought to be associated with dilation of cerebral blood vessels and activation of the trigeminovascular system. During the headache phase of a migraine, CGRP levels are elevated in the cranial venous circulation. Successful amelioration of the headache results in normalization of CGRP levels, thus implicating CGRP in the pathophysiology of this disorder. Moreover, intravenous administration of CGRP to migraineurs induces a delayed migrainous headache in some patients. These observations suggest that inhibition of CGRP-mediated vasodilation may have therapeutic utility in the treatment of migraine headaches, and including but not limited to additional indication described herein.

Aiyar, et al.(1996, *J. Biol. Chem.* 271: 11325–11329) disclose the gene encoding the human calcitonin receptor-like receptor (hCRLR).

McLatchie, et al. (1998, *Nature* 393: 333–339) disclose the gene encoding the human receptor-activity modifying proteins (hRAMP1).

Luebke, et al. (1996, *Proc. Natl. Acad. Sci., USA* 93: 3455–3460) disclose the gene encoding the human receptor component protein (hRCP).

The heterodimeric CGRP receptor requires co-expression of calcitonin receptor-like receptor (CRLR) and an accessory protein called receptor activity modifying protein-1, or RAMP1. Several small molecule CGRP receptor antagonists have been shown to exhibit marked species selectivity, with >100-fold higher affinities for the human CGRP receptor than for receptors from other species. CGRP activity is mediated by the $G_s$-coupled G-protein coupled receptor (GPCR), CRLR, which shares 55% homology with the calcitonin receptor. McLatchie et al. (id.) disclose that functional CGRP and adrenomedullin receptors are both derived from CRLR and that the phenotype is determined by co-expression with a particular RAMP. Co-expression of CRLR with RAMP1 results in CGRP receptor pharmacology, while RAMP2 or RAMP3 co-expression produces an adrenomedullin receptor. RAMPs are relatively small (148–175 amino acids) proteins containing a single predicted membrane spanning domain, a large extracellular domain, and a short cytoplasmic domain. The molecular function of RAMPs includes cell-surface targeting and may involve direct ligand binding or indirect modulation of CRLR conformation, or both.

Doods, et al. (2000, *Br. J. Pharmacol.* 129: 420–423) disclose that a known small-molecule antagonist of the CGRP receptor demonstrates high affinity for the human CGRP receptor, with a $K_i$ of 14 pM. Of particular interest was the observation that this compound exhibited 200-fold lower affinity for CGRP receptors from rat, rabbit, dog, and guinea pig, although the affinity for the marmoset receptor was reported to be similar to that for human. These authors then utilized marmoset for in vivo studies to evaluate the utility of BIBN4096BS as a potential anti-migraine agent.

It is desirable to discover new drugs which antagonize the CGRP receptor for the treatment of various disorders, including but not limited to migraine, pain, menopausal hot flash, migraine prophylaxis, chronic tension type headache, cluster headache, neurogenic or chronic inflammation, gastrointestinal disorders, type 2 diabetes, as well as CGRP agonists which may be useful in the treatment of various cardiovascular disorders. To this end, it is imperative to develop a convenient animal model which expresses a CGRP receptor that mimics human CGRP pharmacological profiles, thus allowing for in vivo efficacy and receptor occupancy studies for testing of potential modulators of CGRP receptor activity, especially human CGRP activity. The present invention addresses and meets these needs by disclosing a "humanized" version of mammalian RAMP1. Co-expression of such a RAMP1 mutant with a mammalian form of CRLR results in a CGRP receptor in which small molecule CGRP receptor antagonists display potency similar to that for the human CGRP receptor. Such a mutant will be useful in both various screening assays which are known in the art, such as cell based assays, receptor binding assays and/or radioligand binding assays, as well as the generation of transgenic animals which provide for this humanized CGRP receptor activity.

SUMMARY OF THE INVENTION

The present invention relates to an isolated or purified nucleic acid molecule (polynucleotide) which encodes a humanized version of the receptor-activity-modifying protein1 (RAMP1).

The present invention further relates to non-human animal cells, non-human transgenic animals, such as founders and littermates, especially transgenic "knock-in" animals, wherein the endogenous gene encoding RAMP1 has been engineered (i.e., "humanized") to provide for a CGRP receptor pharmacological profile similar to human CGRP receptor. A preferred transgenic animal for the construction of such a targeted "knock-in" is a mouse.

The present invention relates to isolated or purified mammalian nucleic acid molecules which encode a chimeric, hybrid and/or mutant version of a mammalian RAMP1 protein, wherein such a derivative RAMP1 protein comprises the respective mammalian amino acid sequence at least from about amino acid 1 to amino acid 65 and from about amino acid 113 to about amino acid 148, wherein the region corresponding from about amino acid 66 to amino acid 112 is at least partially derived from the human RAMP1 coding region.

The present invention further relates to isolated or purified mammalian nucleic acid molecules which encode a chimeric, hybrid and/or mutant version of a mammalian RAMP1 protein, wherein such a derivative RAMP1 protein at least comprises a nucleotide change which results in an alteration of amino acid residue 74 to a tryptophan residue, which results in a humanized mammalian form of RAMP1, exemplified herein by, but not limited to, the nucleic acid molecules disclosed as SEQ ID NOs 1, 3, 5 and 7.

The present invention also relates to fragments or portions of a humanized RAMP1 nucleotide sequence which encompasses the region which encodes the "humanizing" amino acid residue, namely the amino acid residue which corresponds to amino acid 74 of the human RAMP1 protein and which has been altered to encode a tryptophan residue in the respective mammalian RAMP1 nucleotide sequence, including but not limited to such fragments generated from SEQ ID NOs 1, 3, 5 and 7 which encompass the region encoding amino acid residue 74, shown herein to be responsible for "humanization" of the expressed mammalian RAMP1 protein.

The present invention also relates to recombinant vectors and recombinant host cells, both prokaryotic and eukaryotic, which have been transformed or transfected to contain the nucleic acid molecules disclosed throughout this specification and which encode a humanized version of a CGRP receptor and associated fragment thereof, substantially purified forms of a humanized version of a CGRP receptor, recombinant membrane fractions comprising these proteins (e.g., active CGRP receptors comprising CRLR and humanized RAMP1 proteins), associated mutant proteins, and methods associated with identifying compounds which specifically modulated human CGRP utilizing the humanized version of CGRP receptor in various assays.

The present invention also relates to a substantially purified form of a humanized RAMP1 protein, including but not limited to a substantially purified, fully processed (including proteolytic processing, glycosylation and/or phosphorylation), mature humanized RAMP1 protein obtained from a recombinant host cell.

The present invention further relates to a substantially purified membrane preparation, partially purified membrane preparation, or cell lysate which has been obtained from a recombinant host cell transformed or transfected with a DNA expression vector which comprises and appropriately expresses a humanized RAMP1 protein. As noted above, it is preferred that such membrane preparations comprise both a respective mammalian CRLR and RAMP1 protein, so as to form an active, humanized CGRP receptor.

The present invention also relates to biologically active fragments and/or mutants of a humanized RAMP1 protein, comprising and/or consisting of the amino acid sequence as set forth in SEQ ID NOs: 2, 4, 6, and/or 8.

The present invention also relates to polyclonal and monoclonal antibodies raised against forms of humanized RAMP1, a biologically active fragment of humanized RAMP1, and/or a CGRP receptor complex which comprises a humanized RAMP1.

The present invention also relates to isolated nucleic acid molecules which encode humanized RAMP1 fusion constructs.

It is an object of the present invention to provide an isolated nucleic acid molecule (including but not limited to SEQ ID NOs: 1, 3, 5, and/or 7) which encodes a humanized version of RAMP1, or fragments, mutants or derivatives of RAMP1, as set forth in SEQ ID NOs: 2, 4, 6 and 8, respectively. Any such polynucleotide includes but is not necessarily limited to nucleotide substitutions, deletions, additions, amino-terminal truncations and carboxy-terminal truncations such that these mutations encode mRNA which express a protein or protein fragment, which upon co-expression with a mammalian CRLR protein, may exhibit pharmacological properties similar to the human CGRP receptor.

It is an especially preferred object of the present invention to provide for non-human transgenic animals wherein a "humanized" version of RAMP1 is co-expressed with endogenous CRLR, or more preferably, a "knock-in" of the humanized transgene (or a portion comprising amino acid residue 74) to replace the complementary endogenous sequence is performed.

It is a further object of the present invention to provide the humanized RAMP1 proteins or protein fragments encoded by the nucleic acid molecules referred to in the preceding paragraph.

It is another object of the present invention to provide recombinant vectors and recombinant host cells which comprise a nucleic acid sequence encoding a humanized version of RAMP1 or a biological equivalent thereof.

It is an object of the present invention to provide a substantially purified form of humanized RAMP1 proteins, including but not limited to those set forth in SEQ ID NOs: 2, 4, 6 and 8.

Is another object of the present invention to provide a substantially purified recombinant form of a humanized version RAMP1 protein which has been obtained from a recombinant host cell transformed or transfected with a DNA expression vector which comprises and appropriately expresses a complete open reading frame of a mammalian RAMP1 gene, including but in no way limited to DNA expression vectors which comprise nucleic acid molecules as set forth in SEQ ID NOs: 1, 3 5, and 7, respectively, resulting in a functional, processed form of the respective humanized RAMP1. As discussed herein, it is preferred that the RAMP1 protein of the present invention be co-expressed with a mammalian form of CRLR. To this end it is further an object of the present invention to provide for substantially purified subcellular membrane preparations, partially purified subcellular membrane preparations, or crude lysates from recombinant cells which comprise pharmacologically active humanized CGRP receptor, which comprises CRLR and humanized RAMP1 of the present invention. It is also preferred that the recombinant host cell be from a eukaryotic host cell line, such as a mammalian cell line.

It is also an object of the present invention to use cells expressing pharmacologically active humanized CGRP receptor or membrane preparations containing pharmacologically active humanized CGRP receptor or a biological equivalent to screen for modulators, preferably selective antagonists, of CGRP activity. Any such protein, protein complex or membrane associated protein receptor may be useful in screening and selecting CGRP antagonists for the treatment of various conditions as mentioned herein.

As used herein, "isolated or purified nucleic acid molecule" means at least 90%, preferably 95%, more preferably 99%, and even more preferably 99.9%, free of other nucleic acids. As used interchangeably with the terms "substantially free from other nucleic acids" or "substantially purified" or "isolated nucleic acid" or "purified nucleic acid" also refer to a DNA molecules which comprises a coding region for a humanized RAMP1 protein that has been purified away from other cellular components. Thus, a humanized RAMP1 DNA preparation that is substantially free from other nucleic acids will contain, as a percent of its total nucleic acid, no more than 10%, preferably no more than 5%, more preferably no more than 1%, and even more preferably no more than 0.1%, of non-humanized RAMP1 nucleic acid molecules. Whether a given humanized RAMP1 preparation is substantially free from other nucleic acids can be determined by such conventional techniques of assessing nucleic acid purity as, e.g., agarose gel electrophoresis combined with appropriate staining methods, e.g., ethidium bromide staining, or by sequencing.

As used herein, "substantially free from other proteins" or "substantially purified" means at least 90%, preferably 95%, more preferably 99%, and even more preferably 99.9%, free of other proteins. Thus, a humanized RAMP1 protein preparation that is substantially free from other proteins will contain, as a percent of its total protein, no more than 10%, preferably no more than 5%, more preferably no more than 1%, and even more preferably no more than 0.1%, of humanized RAMP1 proteins. Whether a given humanized RAMP1 protein preparation is substantially free from other proteins can be determined by such conventional techniques of assessing protein purity as, e.g., sodium dodecyl sulfate polyacrylamide gel electrophoresis (SDS-PAGE) combined with appropriate detection methods, e.g., silver staining or immunoblotting. As used interchangeably with the terms "substantially free from other proteins" or "substantially purified", the terms "isolated humanized RAMP1 protein" or "purified humanized RAMP1 protein" also refer to humanized RAMP1 protein that has been isolated from a natural source. Use of the term "isolated" or "purified" indicates that humanized RAMP1 protein has been removed from its normal cellular environment. Thus, an isolated humanized RAMP1 protein may be in a cell-free solution or placed in a different cellular environment from that in which it occurs naturally. The term isolated does not imply that an isolated humanized RAMP1 protein is the only protein present, but instead means that an isolated humanized RAMP1 protein is substantially free of other proteins and non-amino acid material (e.g., nucleic acids, lipids, carbohydrates) naturally associated with the humanized RAMP1 protein in vivo. Thus, a humanized RAMP1 protein that is recombinantly expressed in a prokaryotic or eukaryotic cell and substantially purified from this host cell which does not naturally (i.e., without intervention) express this RAMP1 protein is of course "isolated humanized RAMP1 protein" under any circumstances referred to herein. As noted above, a humanized RAMP1 protein preparation that is an isolated or purified humanized RAMP1 protein will be substantially free from other proteins will contain, as a percent of its total protein, no more than 10%, preferably no more than 5%, more preferably no more than 1%, and even more preferably no more than 0.1%, of non-humanized RAMP1 proteins.

As used interchangeably herein, "functional equivalent" or "biologically active equivalent" means a protein which does not have exactly the same amino acid sequence as naturally occurring or humanized RAMP1, due to alternative splicing, deletions, mutations, substitutions, or additions, but retains substantially the same biological activity as the respective naturally occurring or humanized RAMP1. Such functional equivalents will have significant amino acid sequence identity with naturally occurring or humanized RAMP1, especially with the presence of the "humanizing" tryptophan codon at amino acid residue 74.

As used herein, the term "functional" is used to describe a gene or protein that, when present in a cell or in vitro system, performs normally as if in a native or unaltered condition or environment. Therefore, a gene which is not functional (i.e., "non-functional", "disrupted", "altered", or the like) will encode a protein which does not function as a wild type, native or non-altered protein, or encodes no protein at all. Such a non-functional gene may be the product of a homologous recombination event as described herein, where a non-functional gene is targeted specifically to the region of the target chromosome which contains a functional form of the gene, resulting in a "knock-out" of the wild type or native gene.

As used herein, a "modulator" is a compound that causes a change in the expression or activity of a mammalian CGRP receptor, such as a human or humanized CGRP receptor, or causes a change in the effect of the interaction of the respective receptor with its ligand(s), or other protein(s), such as an antagonist or agonist.

As used herein, "rodent" relates to a species which is a member of the order Rodentia, having a single pair of upper and lower incisors for gnawing, wherein the teeth grow continuously and a gap is evident between the incisors and grinding molars. Preferred examples include for generation of transgenic animals include, but are not limited to, *Rattus norvegicus, Rattus rattus*, and *Mus musculus*.

As used herein, "rat" relates to animals which from the point of systemic zoology belong to the genus Rattus. The transgenic animals of the present invention may be generated from any species of the genus Rattus, including but not limited to *Rattus norvegicus* and *Rattus rattus*.

As used herein, "mouse" relates to animals which from the point of systemic zoology belong to the genus *Mus*. The transgenic animals of the present invention may be generated from any species of the genus *Mus*, such as the house mouse, *Mus musculus*.

As used herein, "cynomolgous" or "cyno" refers to a non-human primate also referred to as a macaque, from the genus *Macaca*, such as but not limited to *Macaca cynomolgus*.

As used herein, "marmoset" is known to include non-human primates which possess soft fur and claws (instead of nails) on all digits except the great toe, belonging to the family Callithricidae.

As used herein, "pig" is interchangeable with the term "porcine."As used herein, the term "mammalian" will refer to any mammal, including a human being, except in the context of utilizing a—mammalian—RAMP1 sequence to generate a—humanized—RAMP1 protein. In that context, of course, the human sequence is meant to be excluded.

BRIEF DESCRIPTION OF THE FIGURES

FIG. 1 shows the amino acid alignment of human, rat and mouse wild type RAMP1 protein sequences. Amino acid residue 74, underlined and in italics, is the target amino acid for humanization of mammalian RAMP1 protein sequences such as the mouse and rat sequence.

FIG. 4 shows the alignment of amino acids 66–112 of RAMP1 from human, marmoset, rat, mouse and pig. A partial marmoset RAMP1 clone was generated as described in Example 1.

DETAILED DESCRIPTION OF THE INVENTION

Figure 2:
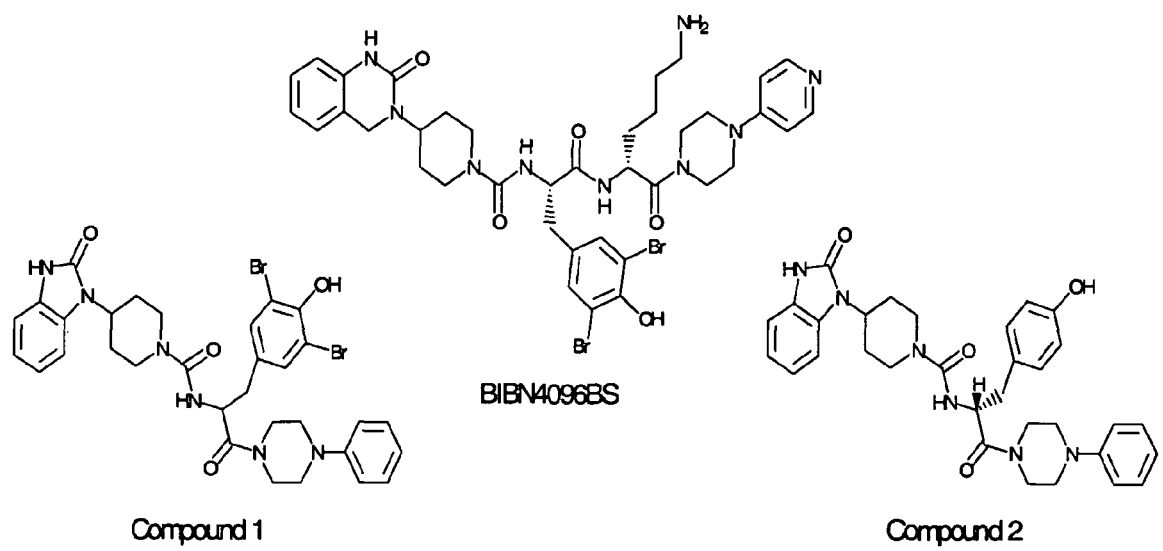
FIG. 2 shows the chemical structure of several CGRP antagonists, BIBN4096BS, Compound 1 and Compound 2.

The present invention relates to an isolated or purified nucleic acid molecule (polynucleotide) which encodes a humanized version of a calcitonin gene-related peptide (CGRP) receptor, which comprises the G-protein coupled receptor calcitonin-receptor-like receptor (CRLR) and the receptor-activity-modifying protein-1 (RAMP1). More specifically, the present invention relates to isolated or purified vertebrate, and preferably mammalian, nucleic acid molecules which encode derivative, humanized versions of the CGRP receptor, namely via DNA molecules which encode chimeric, hybrid or mutant derivatives of a mammalian RAMP1 sequence, which are shown herein to be responsible for the "humanization" of the CGRP receptor upon association with a vertebrate (and again, preferably a mammalian) CRLR receptor protein. The CRLR and RAMP1 DNA molecules disclosed herein may be co-transfected into a host cell of choice wherein the recombinant host cell provides a source for substantial levels of an expressed functional, humanized version of a CGRP receptor. Therefore, these recombinantly expressed humanized CGRP receptor proteins form a receptor complex in which small molecule CGRP receptor antagonists display potency similar to that for a "wild type" human CGRP receptor. Such mutant receptors will be useful in cell based assays, receptor binding assays and/or radioligand binding assays, and, as noted below, in the generation of transgenic animals which provide for this humanized CGRP receptor activity.

To this end, a particularly preferred aspect of the present invention which is afforded only in view of this specification is the generation of non-human animal cells, non-human transgenic animals, such as founders and littermates, especially transgenic "knock-in" animals, wherein the endogenous gene encoding RAMP1 has been engineered (i.e., "humanized") to provide for a CGRP receptor pharmacological profile similar to human CGRP receptor. Such non-human transgenic animals will preferably provide for an altered genotype (endogenous CRLR and "humanized" RAMP1), which will provide for a phenotype whereby the pharmacological profile of the non-human transgenic animal in regard to modulators of CGRP will mimic the human form of CGRP receptor. Various non-human transgenic animals may be contemplated in view of the finding disclosed herein that alteration of a single amino acid residue in a non-human RAMP1 sequence (such as rat, mouse and pig, as shown herein, as well as additional species, such as cyno and canine) results in a "humanized" version of RAMP1 when complexed with a mammalian version of CRLR. In other words, the species-specific pharmacology of known antagonists is shown herein to be localized to the region at or around amino acid residue 74 of human RAMP1 (a tryptophan residue), such that non-human RAMP1 forms may be generated and used to generate transgenic animals which express the humanized version along with or instead of the endogenous RAMP1 protein.

The present invention therefore relates to isolated or purified nucleic acid molecules which encode a chimeric, hybrid and/or mutant version of a RAMP1 protein where such a protein is functional (i.e., when co-expressed with CRLR will exhibit predicted pharmacological properties), and furthermore wherein such a protein is humanized by virtue of altering the amino acid that corresponds to human amino acid residue 74 to a tryptophan residue. Such a nucleic acid molecule is part of the present invention whether it encodes a chimeric, hybrid or various mutant protein, so long as amino acid 74 has been altered from its native residue to the human residue, namely tryptophan.

The present invention further relates to isolated or purified nucleic acid molecules which encode a chimeric, hybrid and/or mutant version of a RAMP1 protein, wherein such a derivative RAMP1 protein comprises the respective amino acid sequence at least from about amino acid 1 to amino acid 65 and from about amino acid 113 to about amino acid 148, wherein the region corresponding from about amino acid 66 to amino acid 112 is at least partially derived from the human RAMP1 coding region. Such DNA molecules will encode "humanized" RAMP1 proteins which, when co-expressed with a CRLR gene, or functional derivative thereof, will result in a CGRP receptor which mimics human CGRP receptor pharmacological properties.

The present invention further relates to isolated or purified nucleic acid molecules which encode a chimeric, hybrid and/or mutant version of a RAMP1 protein, wherein such a derivative RAMP1 protein at least comprises a nucleotide change which results in an alteration of amino acid residue 74 to a tryptophan residue, which results in a humanized form of RAMP1. To this end, a specific embodiment of the present invention relates to an isolated or purified nucleic acid molecule from rat wherein the codon for amino acid residue 74 is altered from a lysine residue to a tryptophan residue. Another specific embodiment of the present invention relates to an isolated or purified nucleic acid molecule from mouse wherein the codon for amino acid residue 74 is altered from a lysine residue to a tryptophan residue. Yet another specific embodiment of the present invention relates to an isolated or purified nucleic acid molecule from cynomolgous wherein the codon for the amino acid residue corresponding to human residue 74 is altered from a cysteine residue to a tryptophan residue (i.e., a "C74W" mutant). Still another specific embodiment of the present invention relates to an isolated or purified nucleic acid molecule from porcine (pig) wherein the codon for the amino acid residue corresponding to human residue 74 is altered from a arginine residue to a tryptophan residue (i.e., a "R74W" mutant). Therefore, the present invention further relates to an isolated nucleic acid molecule (polynucleotide) which encodes mRNA which expresses a humanized RAMP1 protein, this DNA molecule comprising the nucleotide sequence disclosed herein in Table 1 and listed as SEQ ID NO:1 (rat), SEQ ID NO:3 (mouse), SEQ ID NO:5 (a partial sequence from cyno) and SEQ ID NO:7 (a partial sequence from porcine (pig)). Table 1 discloses the nucleotide and predicted amino acid sequences of these various mammalian RAMP1 sequences which, when expressed as a full length RAMP1 protein, correspond to a "humanized" form of RAMP1.

TABLE 1

```
Rat K74W RAMP1 Nucleotide Sequence
ATGGCCCCCG GCCTGCGGGG CCTCCCGCGG CGCGGCCTCT GGCTGCTGCT GGCTCATCAT   (SEQ ID NO:1)

CTCTTCATGG TCACTGCCTG CCGGGACCCT GACTATGGTA CTCTCATCCA GGAGCTGTGT

CTCAGCCGCT TCAAAGAGGA CATGGAGACC ATAGGGAAGA CTCTGTGGTG TGACTCGGGA

AAGACCATAG GGAGCTATGG GGAGCTCACT CACTGCACCT GGCTCGTGGC AAACAAGATT

GGCTGTTTCT GGCCCAATCC GGAAGTGGAC AAGTTCTTCA TTGCTGTCCA CCACCGCTAC

TTCAGCAAGT GCCCAGTCTC GGGCAGGGCC CTGCGGGACC CTCCCAACAG CATCCTCTGC

CCTTTCATTG TGCTCCCCAT TACGGTCACA CTGCTCATGA CTGCCCTGGT GGTCTGGAGG

AGCAAGCGCA CAGAGGGCAT CGTGTAG

Rat K74W RAMP1 Amino Acid Sequence
MAPGLRGLPR RGLWLLLAHH LFMVTACRDP DYGTLIQELC LSRFKEDMET IGKTLWCDWG  (SEQ ID NO:2)

KTIGSYGELT HCTWLVANKI GCFWPNPEVD KFFIAVHHRY FSKCPVSGRA LRDPPNSILC

PFIVLPITVT LLMTALVVWR SKRTEGIV

Mouse K74W RAMP1 Nucleotide Sequence
ATGGCCCCGG GCCTGCGGGG CCTCCCGCGG TGCGGCCTCT GGCTGCTGCT GGCTCACCAT   (SEQ ID NO:3)

CTCTTCATGG TCACTGCCTG CCGGGACCCT GACTATGGGA CTCTCATCCA GGAGCTGTGC

CTCAGCCGCT TCAAGGAGAA CATGGAGACT ATTGGGAAGA CGCTATGGTG TGACTGGGGA

AAGACCATAC AGAGCTATGG GGAGCTCACT TACTGCACCT GGCACGTGGC GCACACGATT

GGCTGTTTCT GGCCCAATCC GGAAGTGGAC AGATTCTTCA TCGCTGTCCA CCATCGATAC

TTCAGCAAGT GCCCCATCTC GGGCAGGGCC CTGCGGGACC CTCCCAACAG CATCCTCTGC

CCTTTCATTG CGCTCCCCAT TACGGTCACG CTGCTCATGA CTGCACTGGT GGTCTGGAGG

AGCAAGCGCA CAGAGGGCAT CGTGTAG

Mouse K74W RAMP1 Amino Acid Sequence
MAPGLRGLPR CGLWLLLAHH LFMVTACRDP DYGTLIQELC LSRFKENMET IGKTLWCDWG  (SEQ ID NO:4)

KTIQSYGELT YCTWHVAHTI GCFWPNPEVD RFFIAVHHRY FSKCPISGRA LRDPPNSILC

PFIALPITVT LLMTALVVWR SKRTEGIV

Cynomolgous RAMP1 Nucleotide Sequence (C74W RAMP1; partial)
GTGCCCTCCT CCAGGAGCTC TGCCTCACCC AGTTCCAGGT AGACATGGAG GCCGTCGGGG   (SEQ ID NO:5)

AGACGCTGTG GTGTGACTGG GGCAGGACCA TCGGGAGCTA CAGGGAGCTG GCCGACTGCA
```

TABLE 1-continued

```
CCTGGCACAT GGCGGAGAAG CTAGGCTGCT TCTGGCCCAA CGCAGAGGTG GACAGGTTCT

TCCTGGCAGT GCACGGGCAC TACTTCAGGG CCTGCCCCAT CTCAGGCAGG GCCGTGCGGG

ACCCGCCTGG CAGCG

Cynomolgous RAMP1 Amino Acid Sequence (C74W RAMP1; partial)
ALLQELCLTQ FQVDMEAVGE TLWCDWGRTI GSYRELADCT WHMAEKLGCF WPNAEVDRFF    (SEQ ID NO:6)

LAVHGHYFRA CPISGRAVRD PPGS

Porcine (Pig) RAMP1 Nucleotide Sequence (R74W RAMP1; partial)
AGGACCATCA GGAGCTATAA AGACCTCTCA GACTGCACCT GGCTCGTGGC GCAAAGGCTG    (SEQ ID NO:7)

GACTGCTTCT GGCCCAACGC GGCGGTGGAC AAGTTCTTCC TGGGAGTCCA CCAGCAGTAC

TTCAGAAACT GCCCCGTCTC CGGCAGGGCC TTGCAGGACC CGCCCAGCAG CGTCCTCTGC

CCCTTCATCG TCGTCCCCAT CCTGGCGACC CTGCTCATGA CCGCACTGGT GGTCTGGCAG

Porcine (Pig) RAMP1 Amino Acid Sequence (R74W RAMP1; partial)
RTIRSYKDLS DCTWLVAQRL DCFWPNAAVD KFFLGVHQQY FRNCPVSGRA LQDPPSSVLC    (SEQ ID NO:8)

PFIVVPILAT LLMTALVVWQ
```

The present invention also relates to biologically active fragments or mutants of SEQ ID NOs:1, 3, 5 and 7 which encode mRNA expressing a humanized RAMP1 protein. Any such biologically active fragment and/or mutant will encode either a protein or protein fragment which at least substantially mimics the pharmacological properties of human RAMP1, including but not limited to the humanized RAMP1 proteins as set forth in SEQ ID NO:2, SEQ ID NO:4, SEQ ID NO:6, and SEQ ID NO:8, with SIDs 6 and 8 representing partial sequences which span the region manipulated for humanization of the respective RAMP1 protein. Any such polynucleotide includes but is not necessarily limited to chimeric constructs (including but not limited to the exemplified chimeric constructs described herein), hybrid constructs, nucleotide substitutions, deletions, additions, amino-terminal truncations and carboxy-terminal truncations such that these mutations encode mRNA which may co-express a functional humanized RAMP1 with a mammalian CRLR protein in a eukaryotic cell so as to be useful for screening for agonists and/or antagonists of CGRP activity. To this end, preferred aspects of this portion of the present invention are disclosed in Table 1 as SEQ ID NOs:1; 3 and 5, all of which encode a humanized version of RAMP1.

The isolated nucleic acid molecules of the present invention may include a deoxyribonucleic acid molecule (DNA), such as genomic DNA and complementary DNA (cDNA), which may be single (coding or noncoding strand) or double stranded, as well as synthetic DNA, such as a synthesized, single stranded polynucleotide. The isolated nucleic acid molecule of the present invention may also include a ribonucleic acid molecule (RNA).

The present invention also relates to recombinant vectors and recombinant host cells, both prokaryotic and eukaryotic, which contain the nucleic acid molecules disclosed throughout this specification and which encode a humanized version of a CGRP receptor and associated fragment thereof, substantially purified forms of associated humanized version of a CGRP receptor, recombinant membrane fractions comprising these proteins (e.g., active CGRP receptors comprising CRLR and humanized RAMP1 proteins), associated mutant proteins, and methods associated with identifying compounds which specifically modulated human CGRP receptor utilizing the humanized version of RAMP1 in various assays.

The present invention also relates to a substantially purified form of a humanized RAMP1 protein, which comprises the amino acid sequence disclosed in Table 1 (e.g., SEQ ID NOs:2, 4, 6 and 8). The invention further relates to a humanized RAMP1 protein which consists of the amino acid sequence disclosed in Table 1 (e.g., SEQ ID NOs:2, 4, 6 and 8). As noted herein, while vertebrate sequences are within the scope of the invention, mammalian sequences, including but not limited to those exemplified herein, are preferred.

Another preferred aspect of the present invention relates to a substantially purified, fully processed (including proteolytic processing, glycosylation and/or phosphorylation), mature humanized RAMP1 protein obtained from a recombinant host cell containing a DNA expression vector comprising nucleotide sequence as set forth in SEQ ID NOs: 1, 3, 5 and 7 which express the respective humanized RAMP1 protein. It is especially preferred that the recombinant host cell be a eukaryotic host cell, such as a mammalian cell line.

Another aspect of the present invention relates to a substantially purified membrane preparation, partially purified membrane preparation, or cell lysate which has been obtained from a recombinant host cell transformed or transfected with a DNA expression vector which comprises and appropriately expresses a complete open reading frame as set forth, for example, in SEQ ID NOs: 1, 3, 5 and 7, which results in a functional form of the respective humanized RAMP1 protein. These recombinant membranes will comprise humanized RAMP1 proteins such as those disclosed in Table 1 (i.e., SEQ ID NOs: 2, 4, 6 and 8), or additional equivalents which results in a humanized form of RAMP1, namely mammalian RAMP1 proteins wherein the amino acid residue corresponding to human amino acid residue 74 has been altered to code for a tryptophan residue.

A preferred aspect of this portion of the present invention relates to a substantially purified membrane preparation, partially purified membrane preparation, or cell lysate which has been obtained from a recombinant host cell transformed or transfected with a DNA expression vector which comprises and appropriately expresses a humanized RAMP1 protein as described throughout this specification, in conjunction with a DNA expression vector which comprises and appropriately expresses a mammalian CRLR GPCR protein. Examples of mammalian nucleotide sequences which may be utilized for such a purpose included but are not limited to the human, rat and mouse nucleic acid molecules disclosed in Table 2 and set forth as SEQ ID NOs: 7, 9, and 11, which results in a functional form of a mammalian CRLR GPCR which, when co-expressed with a humanized RAMP1 protein, will be useful to screen for modulators which effect the human CGRP receptor. The subcellular membrane fractions and/or membrane-containing cell lysates from the recombinant host cells (both prokaryotic and eukaryotic as well as both stably and transiently transformed cells) contain the functional and processed proteins encoded by the nucleic acid molecules disclosed herein. This recombinant-based membrane preparation will comprise a mammalian CRLR protein and a humanized RAMP1 protein which is essentially free from contaminating proteins. These subcellular membrane fractions will comprise "humanized" CGRP receptors which function efficiently for the screening of modulators (e.g., agonists and especially antagonists) of the human CGRP receptor at levels which are at least similar to or possibly substantially above endogenous levels. Any such "humanized" CGRP receptor-containing membrane preparation will be useful in various assays to select for modulators of the respective CGRP receptor. A preferred eukaryotic host cell of choice to express the CGRP receptor of the present invention is a mammalian cell line.

TABLE 2

```
Human CRLR Nucleotide Sequence
ATGGAGAAAA AGTGTACCCT GTATTTTCTG GTTCTCTTGC CTTTTTTTAT GATTCTTGTT  (SEQ ID NO:9)

ACAGCAGAAT TAGAAGAGAG TCCTGAGGAC TCAATTCAGT TGGGAGTTAC TAGAAATAAA

ATCATGACAG CTCAATATGA ATGTTACCAA AAGATTATGC AAGACCCCAT TCAACAAGCA

GAAGGCGTTT ACTGCAACAG AACCTGGGAT GGATGGCTCT GCTGGAACGA TGTTGCAGCA

GGAACTGAAT CAATGCAGCT CTGCCCTGAT TACTTTCAGG ACTTTGATCC ATCAGAAAAA

GTTACAAAGA TCTGTGACCA AGATGGAAAC TGGTTTAGAC ATCCAGCAAG CAACAGAACA

TGGACAAATT ATACCCAGTG TAATGTTAAC ACCCACGAGA AAGTGAAGAC TGCACTAAAT

TTGTTTTACC TGACCATAAT TGGACACGGA TTGTCTATTG CATCACTGCT TATCTCGCTT

CGCATATTCT TTTATTTCAA GAGCCTAAGT TGCCAAAGGA TTACCTTACA CAAAAATCTG

TTCTTCTCAT TTGTTTGTAA CTCTGTTGTA ACAATCATTC ACCTCACTGC AGTGGCCAAC

AACCAGGCCT TAGTAGCCAC AAATCCTGTT AGTTGCAAAG TGTCCCAGTT CATTCATCTT

TACCTGATGG GCTGTAATTA CTTTTGGATG CTCTGTGAAG CCATTTACCT ACACACACTC

ATTGTGGTGG CCGTGTTTGC AGAGAAGCAA CATTTAATGT GGTATTATTT TCTTGGCTGG

GGATTTCCAC TGATTCCTGC TTGTATACAT GCCATTGCTA GAAGCTTATA TTACAATGAC

AATTGCTGGA TCAGTTCTGA TACCCATCTC CTCTACATTA TCCATGGCCC AATTTGTGCT

GCTTTACTGG TGAATCTTTT TTTCTTGTTA AATATTGTAC GCGTTCTCAT CACCAAGTTA

AAAGTTACAC ACCAAGCGGA ATCCAATCTG TACATGAAAG CTGTGAGAGC TACTCTTATC

TTGGTGCCAT TGCTTGGCAT TGAATTTGTG CTGATTCCAT GGCGACCTGA AGGAAAGATT

GCAGAGGAGG TATATGACTA CATCATGCAC ATCCTTATGC ACTTCCAGGG TCTTTTGGTC

TCTACCATTT TCTGCTTCTT TAATGGAGAG GTTCAAGCAA TTCTGAGAAG AAACTGGAAT

CAATACAAAA TCCAATTTGG AAACAGCTTT TCCAACTCAG AAGCTCTTCG TAGTGCGTCT

TACACAGTGT CAACAATCAG TGATGGTCCA GGTTATAGTC ATGACTGTCC TAGTGAACAC

TTAAATGGAA AAAGCATCCA TGATATTGAA AATGTTCTCT TAAAACCAGA AAATTTATAT

AATTGA

Human CRLR Amino Acid Sequence
MEKKCTLYFL VLLPFFMILV TAELEESPED SIQLGVTRNK IMTAQYECYQ           (SEQ ID NO:10)

KIMQDPIQQA EGVYCNRTWD GWLCWNDVAA GTESMQLCPD YFQDFDPSEK

VTKICDQDGN WFRHPASNRT WTNYTQCNVN THEKVKTALN LFYLTIIGHG

LSIASLLISL GIFFYFKSLS CQRITLHKNL FFSFVCNSVV TIIHLTAVAN

NQALVATNPV SCKVSQFIHL YLMGCNYFWM LCEGIYLHTL IVVAVFAEKQ
```

HLMWYYFLGW GFPLIPACIH AIARSLYYND NCWISSDTHL LYIIHGPICA

ALLVNLFFLL NIVRVLITKL KVTHQAESNL YMKAVRATLI LVPLLGIEFV

LIPWRPEGKI AEEVYDYIMH ILMHFQGLLV STIFCFFNGE VQAILRRNWN

QYKIQFGNSF SNSEALRSAS YTVSTISDGP GYSHDCPSEH LNGKSIHDIE

NVLLKPENLY N

Rat CRLR Nucleotide Sequence
ATGGATAAAA AGTGTACACT TTGTTTTCTG TTTCTCTTGC TTCTTAATAT GGCTCTCATC  (SEQ ID NO:11)

GCAGCAGAGT CGGAAGAAGG CGCGAACCAA ACAGACTTGG GAGTCACTAG GAACAAGATC

ATGACGGCTC AGTATGAATG TTACCAAAAG ATCATGCAGG ATCCCATTCA ACAAGGAGAA

GGCCTTTACT GCAACAGAAC CTGGGACGGA TGGCTATGCT GGAATGACGT TGCAGCAGGA

ACCGAGTCAA TGCAGTACTG CCCTGATTAC TTTCAAGATT TTGATCCTTC AGAGAAGGTT

ACAAAGATCT GTGACCAAGA TGGAAACTGG TTCAGACATC CAGATAGTAA CAGGACATGG

ACAAACTACA CCTTGTGTAA CAACAGCACG CATGAGAAAG TGAAGACAGC ACTGAATTTG

TTCTACCTAA CTATAATTGG ACATGGATTA TCTATTGCCT CTCTGATCAT CTCACTCATC

ATATTTTTTT ATTTCAAGAG CCTAAGTTGC CAACGGATTA CATTGCATAA AAACCTGTTC

TTTTCATTTG TTTGTAATTC GATTGTGACA ATCATTCACC TCACGGCAGT GGCCAATAAC

CAGGCCTTAG TGGCCACAAA TCCTGTGAGC TGCAAGGTGT CCCAGTTCAT TCATCTTTAC

CTGATGGGCT GTAACTACTT TTGGATGCTC TGTGAAGGCA TTTACCTGCA CACACTCATT

GTGGTGGCTG TGTTTGCAGA GAAGCAGCAC TTGATGTGGT ATTATTTTCT TGGCTGGGGG

TTTCCTCTGC TTCCTGCCTG CATCCATGCC ATCGCCAGAA GCTTGTATTA CAATGACAAC

TGCTGGATCA GCTCAGACAC TCATCTCCTC TACATCATCC ATGGTCCCAT TTGTGCTGCT

TTACTGGTAA ATCTCTTTTT CCTATTAAAT ATTGTACGTG TTCTCATCAC CAAGTTGAAA

GTTACACACC AAGCAGAATC CAATCTCTAC ATGAAAGCTG TAAGAGCCAC TCTCATCTTG

GTACCACTAC TTGGCATTGA ATTTGTGCTT TTTCCATGGC GGCCTGAAGG AAAGGTTGCT

GAGGAGGTGT ATGACTATGT CATGCACATT CTCATGCACT ATCAGGGTCT TTTGGTGTCT

ACAATTTTCT GCTTCTTTAA CGGAGAGGTT CAAGCAATTC TGAGAAGAAA TTGGAACCAG

TATAAAATCC AATTTGGCAA TGGCTTTTCC CACTCTGATG CTCTCCGCAG CGCATCCTAT

ACGGTGTCAA CAATCAGCGA TGTGCAGGGG TACAGCCACG ACTGCCCCAC TGAACACTTA

AATGGAAAAA GCATCCAGGA TATTGAAAAT GTTGCCTTAA AACCAGAAAA AATGTATGAT

CTAGTGATGT GA

Rat CRLR Amino Acid Sequence
MMDKKCTLCF LFLLLLNMAL IAAESEEGAN QTDLGVTRNK IMTAQYECYQ  (SEQ ID NO:12)

KIMQDPIQQG EGLYCNRTWD GWLCWNDVAA GTESMQYCPD YFQDFDPSEK

VTKICDQDGN WFRHPDSNRT WTNYTLCNNS THEKVKTALN LFYLTIIGHG

LSIASLIISL IIFFYFKSLS CQRITLHKNL FFSFVCNSIV TIIHLTAVAN

NQALVATNPV SCKVSQFIHL YLMGCNYFWM LCEGIYLHTL IVVAVFAEKQ

HLMWYYFLGW GFPLLPACIH AIARSLYYND NCWISSDTHL LYIIHGPICA

ALLVNLFFLL NIVRVLITKL KVTHQAESNL YMKAVRATLI LVPLLGIEFV

LFPWRPEGKV AEEVYDYVMH ILMHYQGLLV STIFCFFNGE VQAILRRNWN

TABLE 2-continued

QYKIQFGNGF SHSDALRSAS YTVSTISDVQ GYSHDCPTEH LNGKSIQDIE

NVALKPEKMY DLVM

Mouse CRLR Nucleotide Sequence
ATGGATAAAA AGCATATACT ATGTTTTCTG GTTCTCTTGC CTCTTAATAT GGCTCTCATC     (SEQ ID NO:13)

TCAGCAGAGT CGGAAGAAGG CGTGAACCAA ACAGACTTGG GAGTCACTAG AAACAAGATC

ATGACGGCTC AATATGAATG TTACCAGAAG ATCATGCAGG ACCCCATTCA ACAAGCAGAA

GGCCTTTACT GCAATAGGAC CTGGGACGGA TGGCTATGCT GGAATGACGT TGCAGCAGGG

ACGGAATCAA TGCAGTACTG CCCTGACTAT TTTCAGGATT TTGATCCTTC AGAGAAGGTT

ACAAAGATCT GTGACCAAGA TGGACACTGG TTTCGGCATC CGGATAGTAA TAGAACATGG

ACCAACTACA CCCTGTGTAA TAACAGCACG CATGAGAAAG TGAAGACAGC CCTGAATCTG

TTCTACCTAA CTATAATTGG ACATGGATTA TCTATTGCAT CTCTGATCAT CTCTCTCATC

ATATTTTTTT ACTTCAAGAG CCTAAGTTGC CAACGGATCA CATTGCATAA AAACCTGTTC

TTTTCATTTA TTTGTAATTC AATTGTAACA ATCATCCACC TCACGGCAGT GGCCAATAAC

CAGGCCTTAG TGGCCACAAA TCCTGTGAGC TGCAAAGTGT CTCAGTTTAT CCATCTCTAC

CTGATGGGCT GTAACTACTT CTGGATGCTC TGTGAAGGCG TTTACCTGCA CACACTCATC

GTGGTGGCTG TGTTTGCGGA GAAGCAGCAC TTGATGTGGT ATTATTTTCT CGGCTGGGGG

TTTCCTCTGC TTCCTGCCTG CATCCACGCC ATTGCCAGAA GCTTGTATTA CAACGACAAT

TGCTCGATCA GCTCAGACAC TCATCTCCTC TACATTATCC ATGGTCCGAT TTGTGCTGCT

TTGTTGGTAA ATCTCTTTTT CCTATTAAAT ATTGTACGTG TTCTCATCAC CAAGTTGAAA

GTTACACACC AAGTGGAATC CAATCTCTAC ATGAAAGCCG TAAGAGCTAC TCTCATCTTG

GTACCACTAC TTGGCATTGA ATTTGTGCTT TTTCCGTGGC GGCCTGAAGG AAAGGTTGCA

GAGGAGGTGT ATGACTATGT CATGCACATT TTGATGCACT TCAGGGTCT TTTGGTGGCT

ACTATTTTCT GCTTCTTTAA TGGAGAGGTT CAAGCAATTC TGAGAAGAAA TTGGAACCAG

TATAAAATCC AATTTGGAAA TGGCTTTTCC CACTCTGATG CTCTCCGCAG TGCATCCTAC

ACAGTGTCAA CAATCAGTGA CATGCAAGGG TACAGCCATG ACTGCCCCAC TGAACACTTA

AATGGAAAAA GCATCCAGGA TATTGAAAAT GTTGCCTTAA AATCAGAAAA TATGTATGAT

CTAGTGATGT GA

Mouse CRLR Amino Acid Sequence
MDKKHILCFL VLLPLNMALI SAESEEGVNQ TDLGVTRNKI MTAQYECYQK     (SEQ ID NO:14)

IMQDPIQQAE GLYCNRTWDG WLCWNDVAAG TESMQYCPDY FQDFDPSEKV

TKICDQDGHW FRHPDSNRTW TNYTLCNNST HEKVKTALNL FYLTIIGHGL

SIASLIISLI IFFYFKSLSC QRITLHKNLF FSFICNSIVT IIHLTAVANN

QALVATNPVS CKVSQFIHLY LMGCNYFWML CEGVYLHTLI VVAVFAEKQH

LMWYYFLGWG FPLLPACIHA IARSLYYNDN CWISSDTHLL YIIHGPICAA

LLVNLFFLLN IVRVLITKLK VTHQVESNLY MKAVRATLIL VPLLGIEFVL

FPWRPEGKVA EEVYDYVMHI LMHFQGLLVA TIFCFFNGEV QAILRRNWNQ

YKIQFGNGFS HSDALRSASY TVSTISDMQG YSHDCPTEHL NGKSIQDIEN

VALKSENMYD LVM

The present invention also relates to biologically active fragments and/or mutants of a humanized RAMP1 protein, comprising the amino acid sequence as set forth in SEQ ID NOs: 2, 4, 6 or 8, including but not necessarily limited to amino acid substitutions, deletions, additions, amino terminal truncations and carboxy-terminal truncations such that these mutations provide for proteins or protein fragments of diagnostic, therapeutic or prophylactic use and would be useful for screening for selective modulators, including but not limited to agonists and/or antagonists for human CGRP receptor pharmacology.

A preferred aspect of the present invention is disclosed in Table 1 as SEQ ID NOs:2, 4, 6 and 8, respective amino acid sequences which are mammalian RAMP1 proteins, or portions thereof, which have been "humanized" solely by altering amino acid residue 74 to a tryptophan ("Trp" or "W") residue. As noted above, co-expression of a humanized RAMP1 protein of the present invention along with a mammalian CRLR protein will be useful in screening for antagonists of the CGRP receptor.

The present invention also relates to polyclonal and monoclonal antibodies raised against forms of humanized RAMP1, a biologically active fragment of humanized RAMP1, or a CGRP receptor complex which comprises a humanized RAMP1.

The present invention also relates to isolated nucleic acid molecules which encode humanized RAMP1 fusion constructs (as well as the substantially purified protein expressed within and recovered from the respective host cell which houses the fusion construct, most likely in the form of a DNA expression vector), including but not limited to fusion constructs which express a portion of humanized RAMP1 to various markers, including but in no way limited to GFP (Green fluorescent protein), the MYC epitope, GST, Fc, Flag, HA, and His-tag. Any such fusion construct will comprise at least a portion of the RAMP1 open reading frame which encodes for the alteration at amino acid 74 to a tryptophan residue, such that the respective fusion protein will exhibit human-like pharmacological properties when complexed with a mammalian CRLR protein.

As noted above, the heterodimeric CGRP receptor requires co-expression of calcitonin receptor-like receptor (CRLR) and an accessory protein called receptor activity modifying protein 1, or RAMP1. Several small molecule CGRP receptor antagonists have been shown to exhibit marked species selectivity, with >100-fold higher affinities for the human CGRP receptor than for receptors from other species. It is shown herein that species selectivity of CGRP modulators is determined exclusively by RAMP1. By constructing hybrid human/rat CRLR/RAMP1 receptors, it is disclosed herein that co-expression of hCRLR with rRAMP1 produced rat receptor pharmacology, and vice versa (h=human, r=rat, m=mouse). Moreover, with rat/human RAMP1 chimeras and site-directed mutants, it is further disclosed herein that a single amino acid at position 74 of the RAMP1 protein modulates the affinity of small molecule antagonists for CRLR/RAMP1. Co-expression of rCRLR with rK74W RAMP1 and mCRLR with mK74W RAMP1 increased the affinities of these antagonists by >100-fold, resulting in $IC_{50}$ values similar to those observed for the human receptor. Therefore, it is disclosed herein that the affinities of small molecule antagonists for the CGRP receptor are heavily influenced by the nature of amino acid 74 of RAMP1 and provide evidence that RAMP1 participates in the antagonist binding sites.

It is shown herein that amino acid position 74 of RAMP1 is responsible for the observed species selectivity of several known antagonists of the CGRP receptor, suggesting that that the affinity of small molecule antagonists can be affected by a single amino acid change and that these antagonists may interact directly with RAMP1. The identification of a single amino acid mutation that can convert the mouse CGRP receptor into one that displays human-like pharmacology shows that a humanized CGRP receptor mouse may be created by a "knock-in" strategy, wherein lysine-74 is replaced with tryptophan by various techniques well known in the art. Such a humanized non-human transgenic animal (e.g., a transgenic mouse), will have utility in drug discovery and development programs for in vivo pharmacological studies of CGRP receptor antagonists, as well as complementing marmoset as a suitable animal model for such studies.

To this end, the present invention relates to a transgenic non-human animal, such as a founder animal or subsequent littermate, wherein both alleles of the endogenous RAMP1 gene have been humanized, as well as heterozygous transgenic non-human animals wherein a single endogenous RAMP1 allele has been humanized and to non-human transgenic animal comprising wild type endogenous RAMP1 alleles in addition to at least one humanized RAMP1 allele stably integrated within the respective target genome. To this end, the present invention relates to animal cells, non-human transgenic embryos, non-human transgenic animals and non-human transgenic littermates which are homozygous for humanized RAMP1 and whereby endogenous RAMP1 has been disrupted, namely by replacement of the endogenous RAMP1 coding region, or portion thereof, by direct gene targeting within the respective target genome. The present invention also extends to animal cells, non-human transgenic embryos, non-human transgenic animals (such as founder animals and transgenic littermates) which are heterozygous for a functional RAMP1 gene native to that animal. Namely, the heterozygosity referring the one functional, endogenous RAMP1 gene and one functional, humanized RAMP1 gene. Also, the present invention relates to animal cells, non-human transgenic embryos and non-human transgenic littermates having at least one and possibly multiple humanized RAMP1 genes being randomly inserted within the target genome, such that both functional endogenous and humanized RAMP1 proteins may be expressed. The transgenic animals of the present invention can be used in the study of the effect of modulators, especially antagonists, of the CGRP receptor. Such a transgenic non-human animal will be especially useful for in vivo efficacy and receptor occupancy studies for testing of CGRP receptor modulators, especially antagonists, for treatment of various disorders, including but not limited to migraine headaches, pain, menopausal hot flash, migraine prophylaxis, chronic tension type headache, cluster headache, neurogenic or chronic inflammation, gastrointestinal disorders, type 2 diabetes and cardiovascular disorders (via agonizing the CGRP receptor). Generation of a genetically engineered mouse expressing a human-like mutant RAMP1 will result in a species in which small molecule CGRP receptor antagonists display potency similar to that for the human CGRP receptor. The non-human transgenic animal of the present invention may also provide cells for culture, for in vitro studies. Therefore, in particular embodiments of the present invention, cell lines are produced and cells isolated from any of the animals produced in the steps described herein.

An aspect of this portion of the invention is a method to obtain an animal wherein the endogenous RAMP1 gene native to the animal has been replaced by "knock-in" technology such that a humanized form of RAMP1 has replaced the endogenous RAMP1 allele(s). A RAMP1 gene that naturally occurs in the animal is referred to as the native gene, endogenous gene and/or "wild-type" gene. It is preferred that expression of a non-native RAMP1 gene (e.g., a "humanized" RAMP1 gene) take place in a transgenic animal in the absence of a native RAMP1 gene. Such a transgenic "knock-in" non-human animal (such as a transgenic mouse) will be especially useful in animal studies to mimic pharmacology of the human CGRP receptor while utilizing an endogenous CRLR gene and a "humanized" RAMP1 gene. The method includes providing a gene for a humanized form of RAMP1 in the form of a transgene and targeting the transgene into a chromosome of the animal at the place of the native RAMP1 gene or at another chromosomal location. The transgene can be introduced into the embryonic stem cells by a variety of methods known in the art, including electroporation, microinjection, and lipofection. Cells carrying the transgene can then be injected into blastocysts which are then implanted into pseudopregnant animals. In alternate embodiments, the transgene-targeted embryonic stem cells can be co-incubated with fertilized eggs or morulae followed by implantation into females. After gestation, the animals obtained are chimeric founder transgenic animals. The founder animals can be used in further embodiments to cross with wild-type animals to produce F1 animals heterozygous for the altered RAMP1 gene. In further embodiments, these heterozygous animals can be interbred to obtain the viable transgenic embryos whose somatic and germ cells are homozygous for the altered, humanized RAMP1. In other embodiments, the heterozygous animals can be used to produce cells lines. In preferred embodiments, the animals are mice or rat. Therefore, a preferred aspect of this portion of the present invention is a transgenic non-human animal which expresses a non-native, humanized RAMP1 protein on a native RAMP1 null background. As noted above, the animal can be heterozygous (i.e., having a different allelic representation of a gene on each of a pair of chromosomes of a diploid genome, such as native RAMP1/humanized RAMP1), homozygous (i.e., having the same representation of a gene on each of a pair of chromosomes of a diploid genome, such as humanized RAMP1/humanized RAMP1) for the altered RAMP1 gene, hemizygous (i.e., having a gene represented on only one of a pair of chromosomes of a diploid genome, preferably a humanized version of RAMP1), or homozygous for the humanized RAMP1 gene. In preferred embodiments, the animal is a mouse or a rat, with mouse being especially preferred. In a further embodiment, the targeted or randomly inserted humanized RAMP1 gene may be operably linked to a promoter. As used herein, operably linked is used to denote a functional connection between two elements whose orientation relevant to one another can vary. In this particular case, it is understood in the art that a promoter can be operably linked to the coding sequence of a gene to direct the expression of the coding sequence while placed at various distances from the coding sequence in a genetic construct. Further embodiments are cell lines and cells derived from animals of this aspect of the invention.

The non-human transgenic animals of the present invention include non-human mammalian species which are candidates for humanization, including but not limited to transgenic mice, transgenic rats, as well as non-human primates which are candidates for RAMP1 humanization. Transgenic mice are preferred.

The present invention especially relates to analysis of the complex function(s) of the CGRP receptor. The native wild type gene is selectively replaced via targeted gene delivery or it resides within the same genome by random integration of a humanized RAMP1 gene in totipotent ES cells and used to generate the transgenic mice of the present invention. Techniques are available to replace an endogenous homologue or to randomly insert such a homologue into the endogenous genomic background by using known targeted homologous recombination or random integration, respectively, to generated genotypic changes into chromosomal alleles. Therefore, as noted above, the present invention relates to diploid animal cells, non-human transgenic embryos, non-human transgenic animals and non-human transgenic founders and/or transgenic littermates which are heterozygous or homozygous for a disrupted RAMP1 gene and/or insertion of a humanized RAMP1 gene. The cells, embryos and non-human transgenic animals contain two chromosome alleles for humanized RAMP1 wherein at least one of the wild type RAMP1 alleles is mutated such that less than wild-type levels of RAMP1 activity is produced. The diploid cell, embryo or non-human transgenic animal homozygous for a humanized RAMP1 gene, wherein a humanized RAMP1 gene has been targeted to replace the wild type allele, may show at least from about 50%, and preferably about 100% reduction in wild type RAMP1 activity (measured by the loss of "wild type" pharmacological characteristics of the endogenous CGRP receptor) and a concomitant CGRP receptor activity which mimics human CGRP receptor pharmacology, as compared to a wild type diploid cell. A diploid mouse cell, embryo or non-human transgenic mouse generated herein which is heterozygous for a disrupted RAMP1 gene (i.e., wtRAMP1/humanized RAMP1) gene may show at least from about 10% to about 100% reduction in endogenous RAMP1 activity compared to a wild type diploid cell. It is within the purview of the artisan of ordinary skill to use known molecular biology techniques to measure the level of transcription, expression and/or functional CRLR/RAMP1 activity in mouse cell homozygous, heterozygous or hemizygous for a humanized RAMP1 gene. Therefore, the present invention especially relates to analysis of the complex function(s) of the CGRP receptor by generating homozygous, heterozygous or hemizygous transgenic mice and studying how various potential modulators interact within these manipulated animals. In a preferred embodiment, the assay is performed by providing an animal of the present invention (especially a transgenic animal wherein a humanized RAMP1 gene has replaced the endogenous RAMP1 gene at both alleles), exposing the animal to a compound (preferably a potential antagonist of CGRP receptor activity), and measuring the effect of said compound on biochemical and physiological responses related to CGRP activity, or lack thereof. The measurement can be compared to these measurements in a genetically similar or identical animal that is not exposed to the compound.

As introduced above, a type of target cell for transgene introduction is preferably the embryonic stem cell (ES), especially when generating a transgenic mouse, where culturing of ES cells has been particularly successful. ES cells can be obtained from pre-implantation embryos cultured in vitro and fused with embryos (Evans et al., 1981, *Nature* 292: 154–156; Bradley et al., 1984, *Nature* 309: 255–258; Gossler et al., 1986, *Proc. Natl. Acad. Sci. USA* 83: 9065–9069; and Robertson et al., 1986, *Nature* 322: 445–448). Transgenes can be efficiently introduced into the ES cells by a variety of standard techniques such as DNA transfection, microinjection, or by retrovirus-mediated transduction. The resultant transformed ES cells can thereafter be combined with blastocysts from a non-human animal. The introduced ES cells thereafter colonize the embryo and contribute to the germ line of the resulting chimeric animal (Jaenisch, 1988, *Science* 240: 1468–1474). The use of gene-targeted ES cells in the generation of gene-targeted transgenic mice was described in 1987 (Thomas et al., *Cell* 51:503–512, (1987)) and is reviewed elsewhere (Frohman et al., *Cell* 56:145–147 (1989); Capecchi, *Trends in Genet.* 5:70–76 (1989); Baribault et al., *Mol. Biol. Med.* 6:481–492, (1989); Wagner, *EMBO J.* 9:3025–3032 (1990); Bradley et al., *Bio/Technology* 10:534–539 (1992)). See also, U.S. Pat. No. 5,464,764, issued to Cappecchi and Thomas on Nov. 7, 1995; U.S. Pat. No. 5,789,215, issued to Berns et al on Aug. 4, 1998, both of which are hereby incorporated by reference). Therefore, techniques are available in the art to generate the transgenic animal cells, non-human transgenic embryos, non-human transgenic animals and non-human transgenic littermates of the present invention. The methods for evaluating the targeted recombination events as well as the resulting knockout mice are also readily available and known in the art. Such methods include, but are not limited to DNA (Southern) hybridization to detect the targeted allele, polymerase chain reaction (PCR), polyacrylamide gel electrophoresis (PAGE), in situ hybridization, RNA/Northern hybridization and Western blots to detect DNA, RNA and protein.

It is now well known in the art that various strategies are readily available to the artisan to generated transgenic animals, such as transgenic "knock-in" animals. For example, BAC recombination technologies, the following of which are expressly incorporated by reference in their entirety, include but are not limited to the teachings of Shizuya, et al., 1992, *Proc. Natl. Acad. Sci. USA* 89: 8794–8797 (introduction of BAC vectors); Zhang et al., 1998, *Nature Genetics* 20: 123–128 and Muyrers, et al., 2001, *Nucleic Acids Research* 27(6): 1555–1557 (modification of BAC clones via plasmid based expression of recA/recT proteins from the Rac phage or radα or radβ from λ phage, respectively, for a review see also Muyrers et al. 2001, *Trends in Biochemical Sciences* 26(5): 325–331); Yu et al. 2000, *Proc. Natl. Acad. Sci. USA* 97(11): 5978–5983 and Lee et al., 2001, *Genomics* 73: 56–65 (use of a defective λ prophage to provide for radα or radβ proteins to promote BAC-based recombination). These technologies allow for the efficient engineering and manipulation of BAC clones to generate an appropriate targeting vector delivery to and recombination within ES cells or harvested pronuclie. It is also known that techniques are readily available that promote site specific recombination, allowing for precise chromosome and transgene engineering. For a review of two well known systems, the FLP recombinase from yeast and Cre recombinase system from bacteriophage P1, see Kilby et al., 1993, *Trends Genetics* 9: 413–421, as well as U.S. Pat. Nos. 5,654,182; 5,677,177; and 5,885,836 (FLP/frt) and U.S. Pat. No. 4,959317 (Cre/loxP), each U.S. patent which is hereby incorporated by reference in their entirety. Therefore, this technology may be utilized to identify a RAMP1 genomic clone (such as a mouse genomic clone), modifying such a genomic clone so as to humanize the coding sequence (i.e., Lys to Trp at amino acid residue 74; where, for example, in generating a transgenic mouse, the only modification required will be the mutagenesis of 2 nucleotides to change the Lysine (AAG) to a Tryptophan (TGG), which results in introduction of a BstNI restriction site [from CCAAG to CCTGG], which is helpful for screening purposes) and to then deliver and stably incorporate, either by homologous or non-homologous recombination, to an ES cell or pronucleus. To provide guidance in developing a humanized mouse "knock in" strategy, the mouse sequence consortium (MSC) database is queried with RAMP1 nucleotide sequence. An initial search resulted in 2 mouse genomic sequence "hits" which were identified as mouse RAMP1. These 2 hits encoded putative exons 2 and 3 of mouse RAMP1. Putative exons 2 and 3 were found on a 712 bp fragment and a 1339 bp contig of 2 fragments, respectively. Putative exon 3 contains amino acid residue 74. This information can be utilized to design a probe for mouse BAC library screening to obtain putative exon 3 and the surrounding intronic sequence for targeting vector construction. The genomic organization appears to be conserved between human and mouse with intron/exon borders located at similar residues (Derst et al., 2000, *Cytogenet Cell Genet* 90: 115–118).

It will be within the scope of the invention to submit screened compounds which show an in vitro modulation effect on humanized CGRP receptor to in vivo analysis, preferably by administering the compound of interest to either a transgenic or wild-type animal as described herein to measure in vivo effects of the compound on this humanized CGRP receptor and to further measure biological and physiological effects of compound administration on the non-human animal. These in vivo studies may be done either alone or in combination with a known RAMP1.

The transgenic non-human animal models as described herein will be useful to screen any potential modulator of CGRP receptor activity (e.g., antagonists or agonists), including but not necessarily limited to peptides, proteins, or non-proteinaceous organic or inorganic molecules. To this end, the present invention relates to processes for the production of the transgenic animals of the present invention and their offspring and their use for pharmacological testing. The invention further relates to methods of determining the selectivity and activity of potential modulators (especially antagonists) of humanized CGRP receptors expressed within transgenic animals of the present invention by administering a test compound or compounds to the transgenic animal and measuring the effect of the compound on the activity of the humanized CGRP receptor. To this end, the present invention relates to various occupancy assays which may be run in conjunction with the transgenic non-human animals of the present invention.

As used and exemplified herein, a transgene is a genetic construct including a gene. The transgene of interest is incorporated into the target genome of the target cell, thus being introduced into their germ cells and/or somatic cells such that it is stably incorporated and is capable of carrying out a desired function. While a chromosome is the preferred target for stable incorporation of a transgene into the target animal, the term "genome" refers to the entire DNA complement of an organism, including nuclear DNA (chromosomal or extrachromosomal DNA) as well as mitochondrial DNA, which is localized within the cytoplasm of the cell. Thus, the transgenic non-human animal of the present invention will stably incorporate one or more transgenes in either/or of the mouse germ cells or somatic cells (preferably both), such that the expression of the transgene (e.g., a humanized form of mammalian RAMP1) achieves the desired effect of presenting a specific receptor occupancy model for modulators of human RAMP1 as well as providing for an pharmacodynamic animal model system to study the selectivity of test compounds to modulate the human RAMP1 receptor. It is preferable to introduce the transgene into a germ line cell, thereby conferring the ability to transfer the information to offspring. If offspring in fact possess some or all of the genetic information, then they, too, are transgenic animals.

As used herein, the term "animal" may include all mammals, except that when referring to transgenic animals, the use of this term excludes humans. It also includes an individual animal in all stages of development, including embryonic and fetal stages. A "transgenic animal" is an animal containing one or more cells bearing genetic information received, directly or indirectly, by deliberate genetic manipulation at a subcellular level, such as by microinjection, targeted gene delivery such as by homologous recombination, or infection with recombinant virus. As noted above, this introduced DNA molecule (i.e., transgene) can be integrated within a chromosome, or it can be extrachromosomally replicating DNA.

As used herein in reference to transgenic animals of this invention, we refer to "transgenes" and "genes". A gene is a nucleotide sequence that encodes a protein, or structural RNA. The gene and/or transgene may also include genetic regulatory elements and/or structural elements known in the art. As used and exemplified herein, a transgene is a genetic construct including a gene. The transgene is integrated into one or more chromosomes in the cells in an animal by methods known in the art. Once integrated, the transgene is carried in at least one place in the genome, preferably a chromosome, of a transgenic animal.

As used herein, "founder" refers to a transgenic animal which develops from the microinjected egg. The founders are tested for expression of a functional gene by any suitable assay of the gene product.

As used herein, the term "line" refers to animals that are direct descendants of one founder and bearing one transgene locus stably integrated into their germline.

As used herein, the term "inbred line" refers to animals which are genetically identical at all endogenous loci. As used in the art, inbred lines may be used for including reproducibility from one animal to the next, ability to transfer cells or tissue among animals, and the ability to carry out defined genetic studies to identify the role of endogenous genes. Such inbred lines may be developed from such lines wherein the mice that are used for microinjection are members of established inbred strains.

As used herein, the term "genotype" is the genetic constitution of an organism.

As used herein, the term "phenotype" is a collection of morphological, physiological and/or biochemical traits possessed by a cell or organism that results from the interaction of the genotype and the environment. Included in this definition of phenotype is a biochemical trait wherein a non-native transgene has been introduced into the animal, thus altering its the genotypic profile, and whereby expression of this transgene(s) within the animal results in a new pharmacological selectivity to one or more chemical compounds, such a selectivity based on functional expression of the transgene(s) of interest. To this end, the term "phenotypic expression" relates to the expression of a transgene or transgenes which results in the production of a product, e.g., a polypeptide or protein, or alters the expression of the zygote's or the organism's natural phenotype.

The transgene of interest is incorporated into the target genome of the target cell, thus being introduced into their germ cells and/or somatic cells such that it is stably incorporated and is capable of carrying out a desired function. While a chromosome is the preferred target for stable incorporation of a transgene into the target animal, the term "genome" refers to the entire DNA complement of an organism, including nuclear DNA (chromosomal or extra-chromosomal DNA) as well as mitochondrial DNA, which is localized within the cytoplasm of the cell. Thus, as noted previously, the transgenic non-human animals of the present invention will stably incorporate one or more transgenes in either/or of the animal's germ cells or somatic cells (preferably both), such that the expression of the transgene (e.g., a functional, humanized version of RAMP1) achieves the desired effect of presenting a specific receptor occupancy model for modulators of a humanized CGRP receptor as well as providing for an pharmacodynamic animal model system to study the selectivity of test compounds to modulate a humanized CGRP receptor which comprises an endogenous CRLR protein and a humanized RAMP1 protein. It is preferable to introduce the transgene into a germ line cell, thereby conferring the ability to transfer the information to offspring. If offspring in fact possess some or all of the genetic information, then they, too, are transgenic animals.

As used herein, the term "animal" may include all mammals, except that when referring to transgenic animals, the use of this term excludes humans. It also includes an individual animal in all stages of development, including embryonic and fetal stages. A "transgenic animal" is an animal containing one or more cells bearing genetic information received, directly or indirectly, by deliberate genetic manipulation at a subcellular level, such as by microinjection, targeted gene delivery such as by homologous recombination, or infection with recombinant virus. As noted above, this introduced DNA molecule (i.e., transgene) can be integrated within a chromosome, or it can be extrachromosomally replicating DNA. In a preferred aspect of the present invention a targeted "knock-in" is performed whereby a humanized version of RAMP1 is inserted and replaces the endogenous RAMP1 coding region.

The degeneracy of the genetic code is such that, for all but two amino acids, more than a single codon encodes a particular amino acid. This allows for the construction of synthetic DNA that encodes a humanized RAMP1 protein where the nucleotide sequence of the synthetic DNA differs significantly from the nucleotide sequences disclosed herein, as exemplification but not limitations, but still encodes a humanized RAMP1 protein. Such synthetic DNAs are intended to be within the scope of the present invention. If it is desired to express such synthetic DNAs in a particular host cell or organism, the codon usage of such synthetic DNAs can be adjusted to reflect the codon usage of that particular host, thus leading to higher levels of expression of the humanized RAMP1 protein in the host. In other words, this redundancy in the various codons which code for specific amino acids is within the scope of the present invention. Therefore, this invention is also directed to those DNA sequences which encode RNA comprising alternative codons which code for the eventual translation of the identical amino acid, as shown below:

A=Ala=Alanine: codons GCA, GCC, GCG, GCU
C=Cys=Cysteine: codons UGC, UGU
D=Asp=Aspartic acid: codons GAC, GAU
E=Glu=Glutamic acid: codons GAA, GAG
F=Phe=Phenylalanine: codons UUC, UUU
G=Gly=Glycine: codons GGA, GGC, GGG, GGU
H=His=Histidine: codons CAC, CAU
I=Ile=Isoleucine: codons AUA, AUC, AUU
K=Lys=Lysine: codons AAA, AAG
L=Leu=Leucine: codons UUA, UUG, CUA, CUC, CUG, CUU
M=Met=Methionine: codon AUG
N=Asp=Asparagine: codons AAC, AAU
P=Pro=Proline: codons CCA, CCC, CCG, CCU
Q=Gln=Glutamine: codons CAA, CAG R=Arg=Arginine: codons AGA, AGG, CGA, CGC, CGG, CGU
S=Ser=Serine: codons AGC, AGU, UCA, UCC, UCG, UCU
T=Thr=Threonine: codons ACA, ACC, ACG, ACU
V=Val=Valine: codons GUA, GUC, GUG, GUU
W=Trp=Tryptophan: codon UGG
Y=Tyr=Tyrosine: codons UAC, UAU Therefore, the present invention discloses codon redundancy which may result in differing DNA molecules expressing an identical protein. For purposes of this specification, a sequence bearing one or more replaced codons will be defined as a degenerate variation. Another source of sequence variation may occur through RNA editing, as discussed infra. Such RNA editing may result in another form of codon redundancy, wherein a change in the open reading frame does not result in an altered amino acid residue in the expressed protein. Also included within the scope of this invention are mutations either in the DNA sequence or the translated protein which do not substantially alter the ultimate physical properties of the expressed protein. For example, substitution of valine for leucine, arginine for lysine, or asparagine for glutamine may not cause a change in functionality of the polypeptide.

It is known that DNA sequences coding for a peptide may be altered so as to code for a peptide having properties that are different than those of the naturally occurring peptide. Methods of altering the DNA sequences include but are not limited to site directed mutagenesis. Examples of altered properties include but are not limited to changes in the affinity of an enzyme for a substrate or a receptor for a ligand.

"Identity" is a measure of the identity of nucleotide sequences or amino acid sequences. In general, the sequences are aligned so that the highest order match is obtained. "Identity" per se has an art-recognized meaning and can be calculated using published techniques. See, e.g.,: (Computational Molecular Biology, Lesk, A. M., ed. Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds. Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991). While there exists a number of methods to measure identity between two polynucleotide or polypeptide sequences, the term "identity" is well known to skilled artisans (Carillo and Lipton, 1988, *SIAM J Applied Math* 48:1073). Methods commonly employed to determine identity or similarity between two sequences include, but are not limited to, those disclosed in Guide to Huge Computers, Martin J. Bishop, ed., Academic Press, San Diego, 1994, and Carillo and Lipton, 1988, *SIAM J Applied Math* 48:1073. Methods to determine identity and similarity are codified in computer programs. Preferred computer program methods to determine identity and similarity between two sequences include, but are not limited to, GCG program package (Devereux, et al, 1984, *Nucleic Acids Research* 12(1):387), BLASTN, and FASTA (Altschul, et al., 1990, *J Mol. Biol.* 215:403).

As an illustration, by a polynucleotide having a nucleotide sequence having at least, for example, 95% "identity" to a reference nucleotide sequence of SEQ ID NO:1 is intended that the nucleotide sequence of the polynucleotide is identical to the reference sequence except that the polynucleotide sequence may include up to five point mutations or alternative nucleotides per each 100 nucleotides of the reference nucleotide sequence of SEQ ID NO:1. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations or alternative nucleotide substitutions of the reference sequence may occur at the 5' or 3' terminal positions of the reference nucleotide sequence or anywhere between those terminal positions, interspersed either individually among nucleotides in the reference sequence or in one or more contiguous groups within the reference sequence. One source of such a "mutation" or change which results in a less than 100% identity may occur through RNA editing. The process of RNA editing results in modification of an mRNA molecule such that use of that modified mRNA as a template to generate a cloned cDNA may result in one or more nucleotide changes, which may or may not result in a codon change. This RNA editing is known to be catalyzed by an RNA editase. Such an RNA editase is RNA adenosine deaminase, which converts an adenosine residue to an inosine residue, which tends to mimic a cytosine residue. To this end, conversion of an mRNA residue from A to I will result in A to G transitions in the coding and noncoding regions of a cloned cDNA (e.g., see Hanrahan et al, 1999, *Annals New York Acad. Sci.* 868:51–66; for a review see Bass, 1997, *TIBS* 22: 157–162). Similarly, by a polypeptide having an amino acid sequence having at least, for example, 95% identity to a reference amino acid sequence of SEQ ID NO:2 is intended that the amino acid sequence of the polypeptide is identical to the reference sequence except that the polypeptide sequence may include up to five amino acid alterations per each 100 amino acids of the reference amino acid of SEQ ID NO:2. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence of anywhere between those terminal positions, interspersed either individually among residues in the reference sequence or in one or more contiguous groups within the reference sequence. Again, as noted above, RNA editing may result in a codon change which will result in an expressed protein which differs in "identity" from other proteins expressed from "non-RNA edited" transcripts, which correspond directly to the open reading frame of the genomic sequence. Therefore, the concept of nucleic acid sequence identity is applicable to the present invention in the context that variations, other than "humanization" of amino acid residue 74, are within the scope of the present invention so long as those variations do not significantly effect the ability of the respective expressed RAMP1 protein to mimic human RAMP1 when associated with a mammalian CRLR protein.

As stated earlier in this section, the present invention also relates to recombinant vectors and recombinant hosts, both prokaryotic and eukaryotic, which contain the substantially purified nucleic acid molecules disclosed throughout this specification. The nucleic acid molecules of the present invention encoding a RAMP1 protein, in whole or in part, can be linked with other DNA molecules, i.e, DNA molecules to which the RAMP1 coding sequence are not naturally linked, to form "recombinant DNA molecules" which encode a respective RAMP1 protein. The DNA molecules of the present invention can be inserted into vectors which comprise nucleic acids encoding RAMP1 or a functional equivalent. These vectors may be comprised of DNA or RNA; for most cloning purposes DNA vectors are preferred. Typical vectors include plasmids, modified viruses, bacteriophage, cosmids, yeast artificial chromosomes, and other forms of episomal or integrated DNA that can encode a RAMP1 protein. It is well within the purview of the skilled artisan to determine an appropriate vector for a particular gene transfer or other use. Therefore, as with many proteins, it is possible to modify many of the amino acids of RAMP1 protein and still retain substantially the same biological activity as the wild type protein. Thus this invention includes modified RAMP1 polypeptides which have amino acid deletions, additions, or substitutions but that still retain substantially the same biological activity as a respective, corresponding humanized RAMP1 (i.e, wherein amino acid 74 is a tryptophan residue and any other changes do not significantly effect the ability of the altered RAMP1 to mimic human pharmacological characteristics as the human CGRP receptor). It is disclosed herein that the essence of the present invention is the ability to humanize a vertebrate RAMP1 protein by altering the vertebrate RAMP1 amino acid sequence at residue 74 to a tryptophan residue. Therefore, alteration of just a single amino acid resulted in a completely different, and now predictable, pharmacological profile for such a mutated protein. This is a surprising result given that historically it was generally accepted that single amino acid substitutions do not usually alter the biological activity of a protein (see, e.g., *Molecular Biology of the Gene*, Watson et al., 1987, Fourth Ed., The Benjamin/Cummings Publishing Co., Inc., page 226; and Cunningham & Wells, 1989, *Science* 244:1081–1085). To this end, the present invention also discloses that minor additional alterations (such as one, two or several non-silent codon changes) will not effect the humanizing characteristic of a RAMP1 protein with the Trp74 modification, and accordingly, such mutant protein are within the scope of the present invention. Therefore, the present invention includes polypeptides where one or more additional amino acid substitutions has been made in SEQ ID NOs:2, 4, 6, and/or 8, wherein the polypeptides still retain substantially the same biological activity as a corresponding RAMP1 protein. For example, mutation of rat K74W to include a mutation at Lys 103 to a Ser residue. This humanized double mutant shows the same "humanized" pharmacological profile as rat K74W, showing that an additional amino acid substitution does not deleteriously effect the ability of the K74W to "humanize" the RAMP1 protein. The present invention also includes polypeptides where two or more amino acid substitutions have been made in SEQ ID NOs:2, 4, 6, or 8, wherein the polypeptides still retain substantially the same biological activity as a corresponding RAMP1 protein. In particular, the present invention includes embodiments where the above-described substitutions are conservative substitutions. To this end, one of ordinary skill in the art would also recognize that polypeptides that are functional equivalents of RAMP1 and have changes from the RAMP1 amino acid sequence that are small deletions or insertions of amino acids could also be produced by following the same guidelines, (i.e, minimizing the differences in amino acid sequence between RAMP1 and related proteins. Small deletions or insertions are generally in the range of about 1 to 5 amino acids. The effect of such small deletions or insertions on the biological activity of the modified RAMP1 polypeptide can easily be assayed by producing the polypeptide synthetically or by making the required changes in DNA encoding RAMP1 and then expressing the DNA recombinantly and assaying the protein produced by such recombinant expression. For instance, as long as amino acid residue 74 remains in a "humanized" form (i.e., Trp), then minor modifications to the remainder of the RAMP1 sequence may be generated and are in turn easily tested alongside an expressed CRLR receptor to determine if the expected human pharmacological profile remains. Furthermore, the present invention also includes truncated forms of RAMP1. Such truncated proteins are useful in various assays described herein, for crystallization studies, and for structure-activity-relationship studies.

The present invention also relates to isolated nucleic acid molecules which are fusion constructions expressing fusion proteins useful in assays to identify compounds which modulate wild-type RAMP1 activity, as well as generating antibodies against RAMP1. One aspect of this portion of the invention includes, but is not limited to, glutathione S-transferase (GST)-RAMP1 fusion constructs. Recombinant GST-RAMP1 fusion proteins may be expressed in various expression systems, including *Spodoptera frugiperda* (Sf21) insect cells (Invitrogen) using a baculovirus expression vector (pAcG2T, Pharmingen). Another aspect involves RAMP1 fusion constructs linked to various markers, including but not limited to GFP (Green fluorescent protein), the MYC epitope, His-tag, and GST. Again, any such fusion constructs may be expressed in the cell line of interest and used to screen for modulators of one or more of the RAMP1 proteins disclosed herein, as well as being expressed and purified.

Any of a variety of procedures may be used to clone and generate a vertebrate or mammalian RAMP1, such as rat, mouse, human, etc., RAMP1. These methods include, but are not limited to, (1) a RACE PCR cloning technique (Frohman, et al., 1988, *Proc. Natl. Acad. Sci. USA* 85: 8998–9002). 5' and/or 3' RACE may be performed to generate a full-length cDNA sequence. This strategy involves using gene-specific oligonucleotide primers for PCR amplification of RAMP1 cDNA. These gene-specific primers are designed through identification of an expressed sequence tag (EST) nucleotide sequence which has been identified by searching any number of publicly available nucleic acid and protein databases; (2) direct functional expression of the RAMP1 cDNA following the construction of a RAMP1-containing cDNA library in an appropriate expression vector system; (3) screening a RAMP1-containing cDNA library constructed in a bacteriophage or plasmid shuttle vector with a labeled degenerate oligonucleotide probe designed from the amino acid sequence of the RAMP1 protein; (4) screening a RAMP1-containing cDNA library constructed in a bacteriophage or plasmid shuttle vector with a partial cDNA encoding the RAMP1 protein. This partial cDNA is obtained by the specific PCR amplification of RAMP1 DNA fragments through the design of degenerate oligonucleotide primers from the amino acid sequence known for other proteins which are related to the RAMP1 protein; (5) screening a RAMP1-containing cDNA library constructed in a bacteriophage or plasmid shuttle vector with a partial cDNA or oligonucleotide with homology to a RAMP1 protein. This strategy may also involve using gene-specific oligonucleotide primers for PCR amplification of RAMP1 cDNA identified as an EST as described above; or (6) designing 5' and 3' gene specific oligonucleotides using any of the disclosed mammalian RAMP1 sequences as a template so that either the full-length cDNA may be generated by known RACE techniques, or a portion of the coding region may be generated by these same known RACE techniques to generate and isolate a portion of the coding region to use as a probe to screen one of numerous types of cDNA and/or genomic libraries in order to isolate a full-length version of the nucleotide sequence encoding RAMP1. It is readily apparent to those skilled in the art that other types of libraries, as well as libraries constructed from other cell types-or species types, may be useful for isolating a RAMP1-encoding DNA or a RAMP1 homologue. Other types of libraries include, but are not limited to, cDNA libraries derived from other brown dog tick cell types.

It is readily apparent to those skilled in the art that suitable cDNA libraries may be prepared from cells or cell lines which have RAMP1 activity. The selection of cells or cell lines for use in preparing a cDNA library to isolate a cDNA encoding RAMP1 may be done by first measuring cell-associated RAMP1 activity using any known assay available for such a purpose.

Preparation of cDNA libraries can be performed by standard techniques well known in the art. Well known cDNA library construction techniques can be found for example, in Sambrook et al., 1989, *Molecular Cloning: A Laboratory Manual*; Cold Spring Harbor Laboratory, Cold Spring Harbor, N.Y. Complementary DNA libraries may also be obtained from numerous commercial sources, including but not limited to Clontech Laboratories, Inc. and Stratagene.

This invention also includes vectors containing a humanized RAMP1 gene, host cells containing the vectors, and methods of making substantially pure humanized RAMP1 protein comprising the steps of introducing the humanized RAMP1 gene into a host cell, and cultivating the host cell under appropriate conditions such that humanized RAMP1 is produced. The humanized RAMP1 so produced may be harvested from the host cells in conventional ways. Therefore, the present invention also relates to methods of expressing the humanized RAMP1 protein and biological equivalents disclosed herein, assays employing these gene products, recombinant host cells which comprise DNA constructs which express these proteins, and compounds identified through these assays which act as agonists or antagonists of humanized RAMP1 activity.

The cloned humanized RAMP1 cDNA obtained through the methods described above may be recombinantly expressed by molecular cloning into an expression vector (such as pcDNA3.neo, pcDNA3.1, pCR2.1, pBlueBacHis2, pLITMUS28, the pIRES series from Clontech, as well as other examples, listed infra) containing a suitable promoter and other appropriate transcription regulatory elements, and transferred into prokaryotic or eukaryotic host cells to produce recombinant humanized RAMP1. Expression vectors are defined herein as DNA sequences that are required for the transcription of cloned DNA and the translation of their mRNAs in an appropriate host. Such vectors can be used to express eukaryotic DNA in a variety of hosts such as bacteria, blue green algae, plant cells, insect cells and animal cells. Specifically designed vectors allow the shuttling of DNA between hosts such as bacteria-yeast or bacteria-animal cells. An appropriately constructed expression vector should contain: an origin of replication for autonomous replication in host cells, selectable markers, a limited number of useful restriction enzyme sites, a potential for high copy number, and active promoters. A promoter is defined as a DNA sequence that directs RNA polymerase to bind to DNA and initiate RNA synthesis. A strong promoter is one which causes mRNAs to be initiated at high frequency. To determine the humanized RAMP1 cDNA sequence(s) that yields optimal levels of humanized RAMP1, cDNA molecules including but not limited to the following can be constructed: a cDNA fragment containing the full-length open reading frame for humanized RAMP1 as well as various constructs containing portions of the cDNA encoding only specific domains of the protein or rearranged domains of the protein. All constructs can be designed to contain none, all or portions of the 5' and/or 3' untranslated region of a humanized RAMP1 cDNA. The expression levels and activity of RAMP1 can be determined following the introduction, both singly and in combination, of these constructs into appropriate host cells. Following determination of the humanized RAMP1 cDNA cassette yielding optimal expression in transient assays, this humanized RAMP1 cDNA construct is transferred to a variety of expression vectors (including recombinant viruses), including but not limited to those for mammalian cells, plant cells, insect cells, oocytes, bacteria, and yeast cells. Techniques for such manipulations can be found described in Sambrook, et al., supra, are well known and available to the artisan of ordinary skill in the art. Therefore, another aspect of the present invention includes host cells that have been engineered to contain and/or express DNA sequences encoding the humanized RAMP1. An expression vector containing DNA encoding a humanized RAMP1-like protein may be used for expression of humanized RAMP1 in a recombinant host cell. Such recombinant host cells can be cultured under suitable conditions to produce humanized RAMP1 or a biologically equivalent form. Expression vectors may include, but are not limited to, cloning vectors, modified cloning vectors, specifically designed plasmids or viruses. Commercially available mammalian expression vectors which may be suitable for recombinant humanized RAMP1 expression, include but are not limited to, pcDNA3.neo (Invitrogen), pcDNA3.1 (Invitrogen), pCI-neo (Promega), pLITMUS28, pLITMUS29, pLITMUS38 and pLITMUS39 (New England Bioloabs), pcDNAI, pcDNAIamp (Invitrogen), pcDNA3 (Invitrogen), pMClneo (Stratagene), pXT1 (Stratagene), pSG5 (Stratagene), EBO-pSV2-neo (ATCC 37593) pBPV-1(8-2) (ATCC 37110), pdBPV-MMTneo(342-12) (ATCC 37224), pRSVgpt (ATCC 37199), pRSVneo (ATCC 37198), pSV2-dhfr (ATCC 37146), pUCTag (ATCC 37460), 1ZD35 (ATCC 37565) and the pIRES series (Clontech). Also, a variety of bacterial expression vectors may be used to express recombinant humanized RAMP1 in bacterial cells. Commercially available bacterial expression vectors which may be suitable for recombinant humanized RAMP1 expression include, but are not limited to pCR2.1 (Invitrogen), pET11a (Novagen), lambda gt11 (Invitrogen), and pKK223-3 (Pharmacia). In addition, a variety of fungal cell expression vectors may be used to express recombinant RAMP1 in fungal cells. Commercially available fungal cell expression vectors which may be suitable for recombinant humanized RAMP1 expression include but are not limited to pYES2 (Invitrogen) and Pichia expression vector (Invitrogen). Also, a variety of insect cell expression vectors may be used to express recombinant protein in insect cells. Commercially available insect cell expression vectors which may be suitable for recombinant expression of humanized RAMP1 include but are not limited to pBlueBacIII and pBlueBacHis2 (Invitrogen), and pAcG2T (Pharmingen).

Recombinant host cells may be prokaryotic or eukaryotic, including but not limited to, bacteria such as *E. coli*, fungal cells such as yeast, mammalian cells including, but not limited to, cell lines of bovine, porcine, monkey and rodent origin; and insect cells. For instance, one insect expression system utilizes *Spodoptera frugiperda* (Sf21) insect cells (Invitrogen) in tandem with a baculovirus expression vector (pAcG2T, Pharmingen). Also, mammalian cells which may be suitable and which are commercially available, include but are not limited to, L cells L-M(TK⁻) (ATCC CCL 1.3), L cells L-M (ATCC CCL 1.2), Saos-2 (ATCC HTB-85), HEK 293 (ATCC CRL 1573), Raji (ATCC CCL 86), CV-1 (ATCC CCL 70), COS-1 (ATCC CRL 1650), COS-7 (ATCC CRL 1651), CHO-K1 (ATCC CCL 61), 3T3 (ATCC CCL 92), NIH/3T3 (ATCC CRL 1658), HeLa (ATCC CCL 2), C127I (ATCC CRL 1616), BS-C-1 (ATCC CCL 26), MRC-5 (ATCC CCL 171) CPAE (ATCC CCL 209), and 293 EBNA cells (Invitrogen).

Expression of humanized RAMP1 DNA may also be performed using in vitro produced synthetic mRNA. Synthetic mRNA can be efficiently translated in various cell-free systems, including but not limited to wheat germ extracts and reticulocyte extracts, as well as efficiently translated in cell based systems, including but not limited to microinjection into frog oocytes, with microinjection into frog oocytes being preferred.

Following expression of humanized RAMP1 in a host cell, humanized RAMP1 protein may be recovered to provide humanized RAMP1 protein in active form. Several humanized RAMP1 protein purification procedures are available and suitable for use. Recombinant humanized RAMP1 protein may be purified from cell lysates and extracts by various combinations of, or individual application of salt fractionation, ion exchange chromatography, size exclusion chromatography, hydroxylapatite adsorption chromatography, hydrophobic interaction chromatography, as well as metal chelate chromotography (e.g., for His-tagged proteins). In addition, recombinant humanized RAMP1 protein can be separated from other cellular proteins by use of an immunoaffinity column made with monoclonal or polyclonal antibodies specific for full-length humanized RAMP1 protein, or polypeptide fragments of humanized RAMP1 protein.

Expression of humanized RAMP1 DNA may also be performed using in vitro produced synthetic mRNA. Synthetic mRNA can be efficiently translated in various cell-free systems, including but not limited to wheat germ extracts and reticulocyte extracts, as well as efficiently translated in cell based systems, including but not limited to microinjection into frog oocytes, with microinjection into frog oocytes being preferred.

Following expression of humanized RAMP1 in a host cell, humanized RAMP1 protein may be recovered to provide humanized RAMP1 protein in active form. Several humanized RAMP1 protein purification procedures are available and suitable for use. Recombinant humanized RAMP1 protein may be purified from cell lysates and extracts by various combinations of, or individual application of salt fractionation, ion exchange chromatography, size exclusion chromatography, hydroxylapatite adsorption chromatography and hydrophobic interaction chromatography, and metal chelate chromatography. In addition, recombinant humanized RAMP1 protein can be separated from other cellular proteins by use of an immunoaffinity column made with monoclonal or polyclonal antibodies specific for full-length humanized RAMP1 protein, or polypeptide fragments of humanized RAMP1 protein.

The humanized RAMP1 proteins of the present invention may be generated by techniques known in the art, as shown in Example Sections 1 and 2, for use in an assay procedure with the CRLR GPCR to identify CGRP receptor modulators (e.g., antagonists of CGRP receptor activity. In general, an assay procedure to identify such receptor modulators will contain a humanized CGRP receptor of the present invention, and a test compound or sample which contains a putative CGRP receptor modulator. The test compounds or samples may be tested directly on, for example, purified receptor protein whether native or recombinant, subcellular fractions of receptor-producing cells whether native or recombinant, and/or whole cells expressing the receptor whether native or recombinant. The test compound or sample may be added to the receptor in the presence or absence of a known labeled or unlabelled receptor ligand. For instance, recombinant membrane fractions containing a humanized CRGP receptor can be used to screen for compounds which inhibit binding of $^{125}$I-CGRP to the receptor in a radioligand biding assay. The modulating activity of the test compound or sample may be determined by, for example, analyzing the ability of the test compound or sample to bind to the receptor, activate the receptor, inhibit receptor activity, inhibit or enhance the binding of other compounds to the receptor, modify receptor regulation, or modify an intracellular activity.

The present invention is also directed to methods for screening for compounds which modulate the expression of DNA or RNA encoding a humanized CGRP receptor as well as the function of a humanized CGRP receptor in vivo. Compounds which modulate these activities may be DNA, RNA, peptides, proteins, or non-proteinaceous organic molecules. Compounds may modulate by increasing or attenuating the expression of DNA or RNA encoding CRLR and/or humanized RAMP1 receptor respectively, or the function either protein. Compounds that modulate the expression of DNA or RNA encoding the CGRP receptor or the function of this receptor may be detected by a variety of assays. The assay may be a simple "yes/no" assay to determine whether there is a change in expression or function. The assay may be made quantitative by comparing the expression or function of a test sample with the levels of expression or function in a standard sample.

The following examples are presented by the way of illustration and, because various other embodiments will be apparent to those in the art, the following is not to be construed as a limitation on the scope of the invention.

EXAMPLE 1

Characterization of Various Mammalian and Humanized RAMP1 cDNAs

Marmoset and Cynomolgous RAMP1 cDNA Cloning—A partial marmoset RAMP1 cDNA and cynomolgous cDNA were isolated from frontal brain cDNA using the polymerase chain reaction (PCR). The PCR primers were based upon human RAMP1 (5'-CTGCCAGGAGGCTAACTACG-3' [SEQ ID NO:25] and 5'-CACGATGAAGGGGTAGAGGA-3' [SEQ ID NO:26]). Amplification reactions consisted of 40 cycles of 45 sec at 94° C., 45 sec at 58° C., and 1 min at 72° C. and were carried out according to the manufacturer's recommended protocol for PLATINUM Taq PCR DNA polymerase (Invitrogen). Multiple subclones were sequenced to rule out potential errors.

Expression Constructs, Chimeras, and Mutagenesis—Human and rat cDNAs for CRLR were subcloned as 5'NheI and 3'NotI fragments into pcDNA3.1/Zeo$^{(+)}$ (Invitrogen). Human RAMP1 (hRAMP1) was provided in the expression vector pcDNA3.1$^{(+)}$ (Invitrogen). Rat RAMP1 (rRAMP1) cloning was as disclosed in Oliver et al., 2001, *Eur. J. Neuroscience* 14: 618–628, hereby incorporated by reference. The cDNA was subcloned as a 5'NotI and 3'BamHI fragment into pcDNA3.1/Hygro(−) (Invitrogen). Table 3 shows various wild type mammalian RAMP1 nucleotide and amino acid sequences. FIG. 4 also shows an alignment of amino acid sequences through the "humanizing residue" at residue #74, including human and marmoset (Trp), rat and mouse (Lys, which may be mutagenized to Trp) and pig (Arg, which may be mutaginized to Trp). FIG. 1 shows the alignment of the full length amino acid sequences for human, rat and mouse RAMP1.

TABLE 3

```
Human RAMP1 Nucleotide Sequence
ATGGCCCGGG CCCTGTGCCG CCTCCCGCGG CGCGGCCTCT GGCTGCTCCT GGCCCATCAC  (SEQ ID NO:15)

CTCTTCATGA CCACTGCCTG CCAGGAGGCT AACTACGGTG CCCTCCTCCG GGAGCTCTGC

CTCACCCAGT TCCAGGTAGA CATGGAGGCC GTCGGGGAGA CGCTGTGGTG TGACTGGGGC

AGGACCATCA GGAGCTACAG GGAGCTGGCC GACTGCACCT GGCACATGGC GGAGAAGCTG

GGCTGCTTCT GGCCCAATGC AGAGGTGGAC AGGTTCTTCC TGGCAGTGCA TGGCCGCTAC

TTCAGGAGCT GCCCCATCTC AGGCAGGGCC GTGCGGGACC CGCCCGGCAG CATCCTCTAC

CCCTTCATCG TGGTCCCCAT CACGGTGACC CTGCTGGTGA CGGCACTGGT GGTCTGGCAG

AGCAAGCGCA CTGAGGGCAT TGTGTAG

Human RAMP1 Amino Acid Sequence
MARALCRLPR RGLWLLLAHH LFMTTACQEA NYGALLRELC LTQFQVDMEA VGETLWCDWG  (SEQ ID NO:16)

RTIRSYRELA DCTWHMAEKL GCFWPNAEVD RFFLAVHGRY FRSCPISGRA VRDPPGSILY

PFIVVPITVT LLVTALVVWQ SKRTEGIV

Rat RAMP1 Nucleotide Sequence
ATGGCCCCCG GCCTGCGGGG CCTCCCGCGG CGCGGCCTCT GGCTGCTGCT GGCTCATCAT  (SEQ ID NO:17)

CTCTTCATGG TCACTGCCTG CCGGGACCCT GACTATGGTA CTCTCATCCA GGAGCTGTGT

CTCAGCCGCT TCAAAGAGGA CATGGAGACC ATAGGGAAGA CTCTGTGGTG TGACTGGGGA

AAGACCATAG GGAGCTATGG GGAGCTCACT CACTGCACCA AACTCGTGGC AAACAAGATT

GGCTGTTTCT GGCCCAATCC GGAAGTGGAC AAGTTCTTCA TTGCTGTCCA CCACCGCTAC

TTCAGCAAGT GCCCAGTCTC GGGCAGGGCC CTGCGGGACC CTCCCAACAG CATCCTCTGC

CCTTTCATTG TGCTCCCCAT TACGGTCACA CTGCTCATGA CTGCCCTGGT GGTCTGGAGG

AGCAAGCGCA CAGAGGGCAT CGTGTAG

Rat RAMP1 Amino Acid Sequence
MAPGLRGLPR RGLWLLLAHH LFMVTACRDP DYGTLIQELC LSRFKEDMET IGKTLWCDWG  (SEQ ID NO:18)

KTIGSYGELT HCTKLVANKI GCFWPNPEVD KFFIAVHHRY FSKCPVSGRA LRDPPNSILC

PFIVLPITVT LLMTALVVWR SKRTEGIV

Mouse RAMP1 Nucleotide Sequence
ATGGCCCCGG GCCTGCGGGG CCTCCCGCGG TGCGGCCTCT GGCTGCTGCT GGCTCACCAT  (SEQ ID NO:19)

CTCTTCATGG TCACTGCCTG CCGGGACCCT GACTATGGGA CTCTCATCCA GGAGCTGTGC

CTCAGCCGCT TCAAGGAGAA CATGGAGACT ATTGGGAAGA CGCTATGGTG TGACTGGGGA

AAGACCATAC AGAGCTATGG GGAGCTCACT TACTGCACCA AGCACGTGGC GCACACGATT

GGCTGTTTCT GGCCCAATCC GGAAGTGGAC AGATTCTTCA TCGCTGTCCA CCATCGATAC

TTCAGCAAGT GCCCCATCTC GGGCAGGGCC CTGCGGGACC CTCCCAACAG CATCCTCTGC

CCTTTCATTG CGCTCCCCAT TACGGTCACG CTGCTCATGA CTGCACTGGT GGTCTGGAGG

AGCAAGCGCA CAGAGGGCAT CGTGTAG

Mouse RAMP1 Amino Acid Sequence
MAPGLRGLPR CGLWLLLAHH LFMVTACRDP DYGTLIQELC LSRFKENMET IGKTLWCDWG  (SEQ ID NO:20)

KTIQSYGELT YCTKHVAHTI GCFWPNPEVD RFFIAVHHRY FSKCPISGRA LRDPPNSILC

PFIALPITVT LLMTALVVWR SKRTEGIV
```

TABLE 3-continued

Cynomolgous RAMP1 Nucleotide Sequence (Partial)
GTGCCCTCCT CCAGGAGCTC TGCCTCACCC AGTTCCAGGT AGACATGGAG GCCGTCGGGG   (SEQ ID NO:21)

AGACGCTGTG GTGTGACTGG GGCAGGACCA TCGGGAGCTA CAGGGAGCTG GCCGACTGCA

CCTGTCACAT GGCGGAGAAG CTAGGCTGCT TCTGGCCCAA CGCAGAGGTG GACAGGTTCT

TCCTGGCAGT GCACGGGCAC TACTTCAGGG CCTGCCCCAT CTCAGGCAGG GCCGTGCGGG

ACCCGCCTGG CAGCG

Cynomolgous RAMP1 Amino Acid Sequence (Partial)
ALLQELCLTQ FQVDMEAVGE TLWCDWGRTI GSYRELADCT CHMAEKLGCF WPNAEVDRFF   (SEQ ID NO:22)

LAVHGHYFRA CPISGRAVRD PPGS

Porcine (Pig) RAMP1 Nucleotide Sequence (Partial)
AGGACCATCA GGAGCTATAA AGACCTCTCA GACTGCACCA GGCTCGTGGC GCAAAGGCTG   (SEQ ID NO:23)

GACTGCTTCT GGCCCAACGC GGCGGTGGAC AAGTTCTTCC TGGGAGTCCA CCAGCAGTAC

TTCAGAAACT GCCCCGTCTC CGGCAGGGCC TTGCAGGACC CGCCCAGCAG CGTCCTCTGC

CCCTTCATCG TCGTCCCCAT CCTGGCGACC CTGCTCATGA CCGCACTGGT GGTCTGGCAG

Porcine (Pig) RAMP1 Amino Acid Sequence (Partial)
RTIRSYKDLS DCTRLVAQRL DCFWPNAAVD KFFLGVHQQY FRNCPVSGRA LQDPPSSVLC   (SEQ ID NO:24)

PFIVVPILAT LLMTALVVWQ

Two human/rat chimeric RAMP1 cDNAs were constructed by using restriction fragments of the corresponding native cDNAs. Chimera 1 was created by replacing the nucleotides coding for the first 66 amino acids of rRAMP1 with the corresponding nucleotides of hRAMP1 by using the BsgI restriction site along with a NheI site located in the cloning vector. Chimera 2 was created by replacing the nucleotides coding for the first 112 amino acids of rRAMP1 with the corresponding nucleotides of hRAMP1 by using the SanDI restriction site along with a NheI site located in the cloning vector.

Rat RAMP1 site-directed mutagenesis was performed by using the Quick Change Site-directed Mutagenesis Kit (Stratagene) according to the manufacturer's instructions. Lysine at position 74 of rRAMP1 was replaced with the corresponding human/marmoset amino acid tryptophan utilizing two complementary mutant oligonucleotide primers (5'-CCACTCACTGCACCTGGCTCGTGGCAAACAAG-3' [SEQ ID NO:27] and 5'-CTTGTTTGCCACGAGCCAG-GTGCAGTGAGTGAG-3' [SEQ ID NO:28]) and the rRAMP1 expression vector construct as template. This mutation was accomplished by substituting the codon TGG corresponding to tryptophan (rK74W RAMP1). All constructs were sequenced bidirectionally with 100% coverage in each direction.

Cell Culture and DNA Transfection—293 EBNA cells were cultured in DMEM with 4.5 g/L glucose, 1 mM sodium pyruvate and 2 mM glutamine supplemented with 10% Fetal Bovine Serum (FBS), 100 units/mL penicillin and 100 μg/mL streptomycin, and maintained at 37° C. and 95% humidity. Cells were subcultured by treatment with 0.25% trypsin with 0.1% EDTA in HBSS.

Twenty-four hours prior to transfection, the cells were seeded at $2.0 \times 10^7$/dish in 500 cm$^2$ dishes. The following day, the cells were re-fed with fresh growth medium 1 hour before transfection. Transfections were performed by combining 60 μg/dish DNA with 180 μg/dish Lipofectamine 2000 (Life Technologies). cDNA's for CRLR and RAMP1 in the mammalian expression vector pcDNA3.1 were co-transfected in equal amounts. The transfection cocktail was added directly to the medium and this mixture was replaced with fresh medium 24 hours later. The cells were harvested for membranes 48 hours post-transfection.

Membrane Preparation and Radioligand Binding Studies—Transiently transfected 293 EBNA cells were washed once with PBS and harvested in harvest buffer containing 50 mM HEPES, 1 mM EDTA and Complete protease inhibitors (Roche). The cell suspension was disrupted with a laboratory homogenizer and centrifuged at 48000 g to isolate membranes. The pellets were re-suspended in harvest buffer plus 250 mM sucrose. Membranes were stored at −70° C. as aliquots.

For binding assays, 1.5–25 μg of membranes (dependent upon receptor expression levels) were incubated for 3 hours at room temperature in binding buffer (10 mM HEPES, 5 mM MgCl$_2$, 0.2% BSA) containing 10 pM $^{125}$I-hCGRP (Amersham) in a total volume of 1 mL. Similar results were obtained by using $^{125}$I-rCGRP (Amersham). Incubations were terminated by filtration through GF/B 96-well filter plates that had been blocked with 0.5% polyethyleneimine. Non-specific binding was determined by using a final concentration of 100 nM hCGRP (for peptide assays) or 300 nM BIBN4096BS (for small molecule assays). Data were analyzed by using GraphPad Prism. Dose response curves were plotted and IC$_{50}$ values determined from a 4-parameter fit as defined by the equation $y=((a-d)/(1+(x/c)^b))+d$, where y=response, x=dose, a=max response, d=min response, c=inflection point and b=slope. Data reported in Table 4–6 are from a single experiment, but are representative of 2–3 replicates.

Western Blotting—Membranes expressing rCRLR were treated separately with either Endoglycosidase F1 or Peptide-N-Glycosidase F (Calbiochem) overnight at 37° C. After the addition of protein gel loading buffer, the samples were heated at 70° C. for 10 min, then loaded onto a 4–12% gradient NuPAGE Bis-Tris polyacrylamide gel (Invitrogen).

Following electrophoresis, the separated proteins were transferred to a 0.45 μm nitrocellulose membrane. Rat CRLR was detected by using the WesternBreeze Immunodetection kit (Invitrogen) with affinity purified rabbit anti-rat CRLR (Alpha Diagnostic International).

Results—Small molecule antagonists of the CGRP receptor have been shown to exhibit species selective pharmacology (Doods, et al., 2000, Br. J. Pharmacol. 129, 420–423; Edvinsson, et al., 2001, Eur. J. Pharmacol. 415: 39–44; Hasbak, et al., 2001, Br. J. Pharmacol. 133: 1405–1413). Protein sequence alignment reveals that while human and rat CRLR are 91% homologous, human and rat RAMP1 share only 71% homology. BIBN4096BS was reported to exhibit 200-fold higher affinity for the human CGRP receptor than for the rat receptor (Doods, et al., id.). This observation suggested that the pharmacological differences could be a result of the sequence dissimilarity of either protein, or may result from a combined effect of differences in both CRLR and RAMP1 sequences. In order to first determine if the species selectivity is derived from either CRLR itself, or its accessory protein RAMP1, hybrid human/rat CGRP receptors were created by transiently transfecting cDNA's coding for human CRLR with rat RAMP1 and vice versa in 293 EBNA cells. The cells were harvested and cell membranes were prepared for subsequent competitive ligand binding experiments. As expected, the small molecule antagonists Compound 1 and BIBN4096BS had lower affinity for rCRLR/rRAMP1 than for the transfected human CGRP receptor (Table 4; see FIG. 2 for structure of BIBN4096BS and Compounds 1 and 2). However, the peptide antagonist $CGRP_{8-37}$ displayed similar affinities for CGRP receptors from human and rat, with $IC_{50}$ values of 2.8 and 2.0 nM, respectively. In 293 EBNA membranes expressing rCRLR/rRAMP1, $^{25}$I-hCGRP binding was inhibited by Compound 1 and BIBN4096BS with $IC_{50}$ values of 15,000 and 6.9 nM respectively. In contrast, recombinantly expressed rCRLR/hRAMP1 showed human-like pharmacology toward Compound 1 and BIBN4096BS with $IC_{50}$'s of 190 and 0.41 nM respectively (Table 4). Likewise, the $IC_{50}$ values for Compound 1 and BIBN4096BS for hCRLR/rRAMP1 were similar to those observed for the native rat receptor. These results demonstrated that RAMP1 determines the affinity of BIBN4096BS and Compound 1 for human and rat CGRP receptors. The species origin of CRLR in these hybrid receptors had little or no effect on the small molecule antagonist affinities.

TABLE 4

Summary of competitive binding experiments on membranes expressing mixed species CRLR/RAMP1 receptor complexes. hCRLR and rCRLR were transiently transfected into 293 EBNA cells along with either human or rat RAMP1. Membranes were prepared 48 hours post-transfection.

| | $IC_{50}$, nM | |
|---|---|---|
| | Compound 1 | BIBN4096BS |
| hCRLR/hRAMP1 | 150 | 0.16 |
| rCRLR/rRAMP1 | 15,000 | 6.9 |
| rCRLR/hRAMP1 | 190 | 0.41 |
| hCRLR/rRAMP1 | 24,000 | 6.1 |

Figure 3:
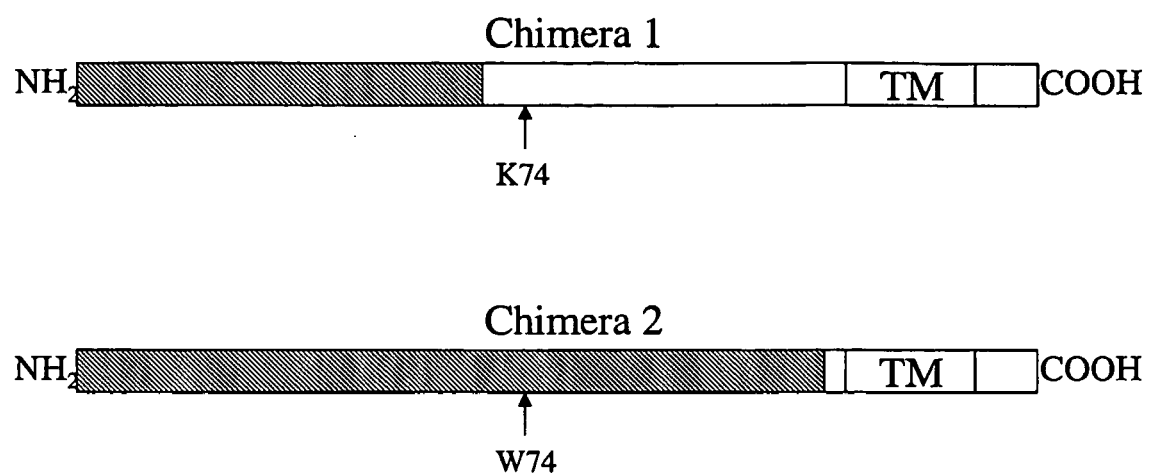
FIG. 3 shows the constructed RAMP1 Chimeras and RAMP1 Mutagenesis. Chimera 1 was constructed by replacing the first 66 amino acids of rat RAMP1 with the human sequence. Chimera 2 was generated in a similar fashion by replacing the first 112 amino acids of rat RAMP1 with those from human RAMP1. Hashed regions indicate human RAMP1 sequence; the remaining unfilled areas represent rat peptide sequence. Mutagenesis of rat RAMP1 at position 74 produced a single RAMP1 point mutant.

RAMPs are accessory proteins predicted to contain a large extracellular N-terminal domain and a single transmembrane (TM) spanning domain. To elucidate the region of RAMP1 that is directly involved in determining the affinities of BIBN4096BS and Compound 1, human/rat RAMP1 chimeras were generated. Chimera 1 was created by replacing the first 66 amino acids of rRAMP1 with the corresponding hRAMP1 sequence (FIG. 3). Conversely, replacement of the first 112 amino acids of rRAMP1 with the human sequence produced Chimera 2. These constructs were then used for transient transfections in similar experiments as described above. In membranes expressing rCRLR with Chimera 1, $^{125}$I-hCGRP binding was inhibited by Compound 1 and BIBN4096BS with $IC_{50}$ values of 9,000 and 4.8 nM respectively (Table 5). These results were similar to those obtained for rCRLR/rRAMP1. By contrast, when rCRLR was co-expressed with Chimera 2, the resulting $IC_{50}$'s were similar to those obtained for hCRLR/hRAMP1. These studies demonstrated that amino acids 66–112 in the extracellular domain of RAMP1 were responsible for modulating the affinity of BIBN4096BS and Compound 1 for CRLR/RAMP1.

TABLE 5

Summary of competitive binding experiments on membranes expressing rCRLR with the RAMP1 Chimeras.

| | $IC_{50}$, nM | |
|---|---|---|
| | Compound 1 | BIBN4096BS |
| hCRLR/hRAMP1 | 150 | 0.16 |
| rCRLR/rRAMP1 | 15,000 | 6.9 |
| rCRLR/Chimera 1 | 9,000 | 4.8 |
| rCRLR/Chimera 2 | 150 | 0.16 |

The identification of amino acids 66–112 of RAMP1 as the critical region determining CGRP receptor pharmacology allows for the possibility that the species selectivity might be governed by specific amino acid residues. A partial marmoset RAMP1 cDNA was cloned and the sequence compared with that from human and the other available RAMP1 sequences. Protein sequence alignment revealed fourteen residues that were identical in human and marmoset but different from that found in rat, mouse and pig (FIG. 4). Amino acid 74 was targeted as a potential mutagenesis target, since the human and marmoset sequences contained tryptophan at this position, but a basic residue was found in the three other species. Subsequently, lysine at position 74 of rRAMP1 was replaced with the corresponding human/marmoset amino acid tryptophan. This construct was then co-transfected with rCRLR in 293 EBNA cells. Competitive binding experiments demonstrated that human-like receptor pharmacology could be rescued by co-expression of rCRLR with rK74W RAMP1 (Table 6). The $IC_{50}$ of BIBN4096BS for rCRLR/rK74W RAMP1 was similar to that observed for hCRLR/hRAMP1, 0.08 versus 0.02 nM, respectively, and was significantly more potent than the affinity for the native rat receptor, 5.5 nM. A similar trend was observed for Compound 2. Compound 1 exhibited >10-fold higher affinity for the rCRLR/rK74W RAMP1 receptor than for the native human receptor, perhaps due to favorable interactions between the dibromotyrosyl moiety and the tryptophan in the RAMP1 mutant. These results suggested that the affinities of these small molecule antagonists for the CGRP receptor were heavily influenced by the nature of amino acid 74 of RAMP1.

TABLE 6

Summary of competitive binding experiments
on membranes expressing rCRLR
and mutant rK74W RAMP1.

| | $IC_{50}$, nM | | |
|---|---|---|---|
| | Compound 1 | Compound 2 | BIBN4096BS |
| hCRLR/hRAMP1 | 270 | 104 | 0.02 |
| rCRLR/rRAMP1 | 20,000 | >20,000 | 5.5 |
| rCRLR/rK74W RAMP1 | 19 | 120 | 0.08 |

Figure 5:
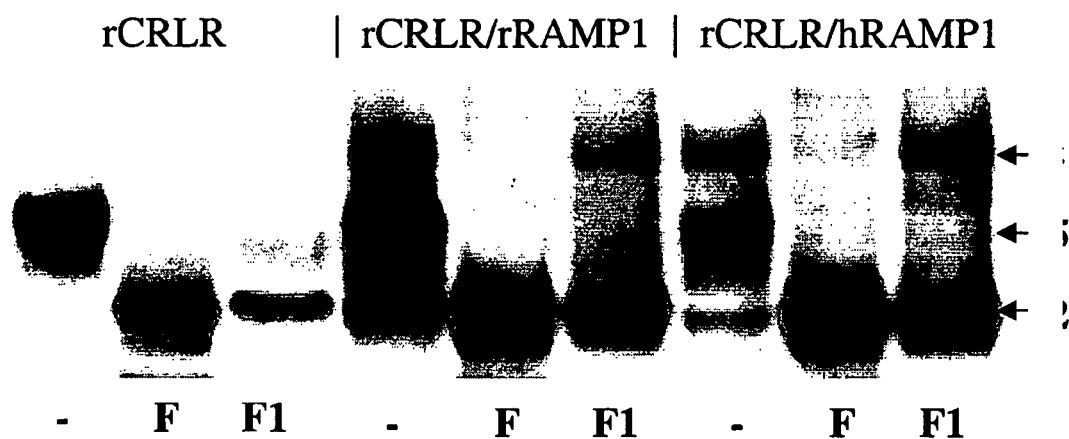
FIG. 5 shows Western blotting analysis of rCRLR co-expressed with rRAMP1(rat RAMP1) and hRAMP1 (human RAMP1). The membranes from the competitive binding experiments, including rCRLR transfected with empty vector (pcDNA3.1), were treated with Peptide-N-Glycosidase F (F), Endoglycosidase F1 (F1), or no enzyme. Samples were separated by SDS-PAGE, followed by western blot analysis with anti-rat CRLR antibodies.

One of the demonstrated functions of RAMPs is to ensure proper cell surface targeting of CRLR. The functional significance of glycosylation was therefore addressed because the glycosylation state of the rat CGRP receptor had not been characterized previously; furthermore, the possibility existed that rat and human RAMP1 resulted in differential glycosylation of CRLR and that this effect determined the observed differences in antagonist affinities. Using an antibody to rCRLR and deglycosylation enzymes, the glycosylation state of rCRLR associated with rat or human RAMP1 was determined. The membranes from the competitive binding experiments (rCRLR/rRAMP1, rCRLR/hRAMP1 and control rCRLR/pcDNA3.1) were treated with Peptide-N-Glycosidase F (PNGase F) and Endoglycosidase F1 (Endo F1). PNGase F catalyzes the hydrolysis of mature glycoproteins, whereas Endo F1 cleaves N-linked high mannose and hybrid oligosaccharides, but not complex oligosaccharides. Thus, the molecular weight of a glycosylated receptor will decrease after treatment with PNGase F and a receptor with complex glycosylation will resist Endo F1 cleavage. Co-expression of rCRLR with either human or rat RAMP1 produced $M_r$ species of 55 and 68 kDa, which were reduced to a single 42 kDa species following PNGase F treatment (FIG. 5). Furthermore, the 68 kDa species represented a mature glycoprotein, as demonstrated by its resistance to Endo F1 cleavage. The negative control rCRLR alone resulted in background levels of the 55 kDa species, possibly resulting from interaction of transfected CRLR with low levels of endogenous RAMP1. The 55 kDa species likely represents a core glycosylated form of the receptor. These results indicated that the co-expression of either human or rat RAMP1 with rat CRLR resulted in similar levels of complex glycosylation.

EXAMPLE 2

A mouse cDNA for CRLR was isolated from mouse brain cDNA using the polymerase chain reaction (PCR). PCR primers (5'-TAGCTAGCGCCACCATGGATAAAAAG-CATATAC [SEQ ID NO:29] and 5'-CGGGATCCTGGC-TATCCAATCTTTTGGC-3' [SEQ ID NO:30]) were based upon Genbank accession number AF209905. Engineered 5'NheI and 3'BamHI sites were utilized for subcloning into the expression vector pcDNA3.1/Hygro(−) (Invitrogen). A mouse cDNA for RAMP1 was isolated from mouse brain cDNA utilizing PCR. PCR primers (5'-ATGCGGC-CGCGTGGGGCTCTGCTTGCCATG-3' [SEQ ID NO:31] and 5'-CGGGATCCCTCATCACCTGGGATACCTAC-3' [SEQ ID NO:32]) were based upon the published mouse RAMP1 sequence (Knut, et al., 2000, Mol. Cell. Endocrinol. 162: 35–43). Engineered 5'NotI and 3'BamHI sites were utilized for subcloning into the expression vector pcDNA3.1/Hygro(−) (Invitrogen). Mouse RAMP1 site-directed mutagenesis was performed by the same method employed in EXAMPLE 1. The mouse RAMP1 expression vector construct was used as template utilizing two complementary mutant oligonucleotide primers (5'-GCTCACT-TACTGCACCTGGCACGTGGCGCACACG [SEQ ID NO:33] and 5'-CGTGTGCGCCACGTGCCAGGTGCAG-TAAGTGAGC [SEQ ID NO:34]). This mutation was accomplished by substituting a TG at positions 1 and 2 of the mouse lysine codon (AAG) resulting in the tryptophan codon TGG (mK74W RAMP1). Cell culture, DNA transfection, membrane preparation, and radioligand biding studies were carried out as in EXAMPLE 1.

Competitive binding experiments demonstrated that human-like receptor pharmacology could be rescued by co-expression of mCRLR with mK74W RAMP1 (Table 7). The $IC_{50}$ of BIBN4096BS for mCRLR/mK74W RAMP1 was similar to that observed for hCRLR/hRAMP1, 0.1 versus 0.02 nM, respectively, and was significantly more potent than the affinity for the native mouse receptor, 8.5 nM. A similar trend was observed for Compound 2. Compound 1 exhibited >10-fold higher affinity for the mCRLR/mK74W RAMP1 receptor than for the native human receptor as was also observed with the rCRLR/rK74W RAMP1 receptor.

TABLE 7

Summary of competitive binding experiments
on membranes expressing mCRLR and
mutant mK74W RAMP1.

| | $IC_{50}$, nM | | |
|---|---|---|---|
| | Compound 1 | Compound 2 | BIBN4096BS |
| hCRLR/hRAMP1 | 150 | 70 | 0.02 |
| mCRLR/mRAMP1 | >20,000 | >20,000 | 8.5 |
| mCRLR/mK74W RAMP1 | 13 | 310 | 0.1 |

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

Various publications are cited herein, the disclosures of which are incorporated by reference in their entireties.

SEQUENCE LISTING

<160> NUMBER OF SEQ ID NOS: 34

<210> SEQ ID NO 1
<211> LENGTH: 447

-continued

<212> TYPE: DNA
<213> ORGANISM: Rattus rattus

<400> SEQUENCE: 1

```
atggccccg gcctgcgggg cctcccgcgg cgcggcctct ggctgctgct ggctcatcat    60
ctcttcatgg tcactgcctg ccgggaccct gactatggta ctctcatcca ggagctgtgt   120
ctcagccgct tcaaagagga catggagacc atagggaaga ctctgtggtg tgactgggga   180
aagaccatag ggagctatgg ggagctcact cactgcacct ggctcgtggc aaacaagatt   240
ggctgtttct ggcccaatcc ggaagtggac aagttcttca ttgctgtcca ccaccgctac   300
ttcagcaagt gcccagtctc gggcagggcc ctgcggga cc ctcccaacag catcctctgc   360
cctttcattg tgctccccat tacggtcaca ctgctcatga ctgccctggt ggtctggagg   420
agcaagcgca cagagggcat cgtgtag                                       447
```

<210> SEQ ID NO 2
<211> LENGTH: 148
<212> TYPE: PRT
<213> ORGANISM: Rattus rattus

<400> SEQUENCE: 2

```
Met Ala Pro Gly Leu Arg Gly Leu Pro Arg Arg Gly Leu Trp Leu Leu
 1               5                  10                  15

Leu Ala His His Leu Phe Met Val Thr Ala Cys Arg Asp Pro Asp Tyr
            20                  25                  30

Gly Thr Leu Ile Gln Glu Leu Cys Leu Ser Arg Phe Lys Glu Asp Met
        35                  40                  45

Glu Thr Ile Gly Lys Thr Leu Trp Cys Asp Trp Gly Lys Thr Ile Gly
    50                  55                  60

Ser Tyr Gly Glu Leu Thr His Cys Thr Trp Leu Val Ala Asn Lys Ile
65                  70                  75                  80

Gly Cys Phe Trp Pro Asn Pro Glu Val Asp Lys Phe Phe Ile Ala Val
                85                  90                  95

His His Arg Tyr Phe Ser Lys Cys Pro Val Ser Gly Arg Ala Leu Arg
            100                 105                 110

Asp Pro Pro Asn Ser Ile Leu Cys Pro Phe Ile Val Leu Pro Ile Thr
        115                 120                 125

Val Thr Leu Leu Met Thr Ala Leu Val Val Trp Arg Ser Lys Arg Thr
    130                 135                 140

Glu Gly Ile Val
145
```

<210> SEQ ID NO 3
<211> LENGTH: 447
<212> TYPE: DNA
<213> ORGANISM: Mus musculus

<400> SEQUENCE: 3

```
atggccccgg gcctgcgggg cctcccgcgg tgcggcctct ggctgctgct ggctcaccat    60
ctcttcatgg tcactgcctg ccgggaccct gactatggga ctctcatcca ggagctgtgc   120
ctcagccgct tcaaggagaa catggagact attgggaaga cgctatggtg tgactgggga   180
aagaccatac agagctatgg ggagctcact tactgcacct ggcacgtggc gcacacgatt   240
ggctgtttct ggcccaatcc ggaagtggac agattcttca tcgctgtcca ccatcgatac   300
ttcagcaagt gccccatctc gggcagggcc ctgcgggacc ctcccaacag catcctctgc   360
```

```
ccttcattg cgctccccat tacggtcacg ctgctcatga ctgcactggt ggtctggagg    420
agcaagcgca cagagggcat cgtgtag                                      447
```

<210> SEQ ID NO 4
<211> LENGTH: 148
<212> TYPE: PRT
<213> ORGANISM: Mus musculus

<400> SEQUENCE: 4

```
Met Ala Pro Gly Leu Arg Gly Leu Pro Arg Cys Gly Leu Trp Leu Leu
1               5                   10                  15

Leu Ala His His Leu Phe Met Val Thr Ala Cys Arg Asp Pro Asp Tyr
                20                  25                  30

Gly Thr Leu Ile Gln Glu Leu Cys Leu Ser Arg Phe Lys Glu Asn Met
            35                  40                  45

Glu Thr Ile Gly Lys Thr Leu Trp Cys Asp Trp Gly Lys Thr Ile Gln
    50                  55                  60

Ser Tyr Gly Glu Leu Thr Tyr Cys Thr Trp His Val Ala His Thr Ile
65                  70                  75                  80

Gly Cys Phe Trp Pro Asn Pro Glu Val Asp Arg Phe Phe Ile Ala Val
                85                  90                  95

His His Arg Tyr Phe Ser Lys Cys Pro Ile Ser Gly Arg Ala Leu Arg
                100                 105                 110

Asp Pro Pro Asn Ser Ile Leu Cys Pro Phe Ile Ala Leu Pro Ile Thr
            115                 120                 125

Val Thr Leu Leu Met Thr Ala Leu Val Val Trp Arg Ser Lys Arg Thr
    130                 135                 140

Glu Gly Ile Val
145
```

<210> SEQ ID NO 5
<211> LENGTH: 255
<212> TYPE: DNA
<213> ORGANISM: Macaca cynomolus

<400> SEQUENCE: 5

```
gtgccctcct ccaggagctc tgcctcaccc agttccaggt agacatggag gccgtcgggg    60
agacgctgtg gtgtgactgg ggcaggacca tcgggagcta cagggagctg gccgactgca   120
cctggcacat ggcggagaag ctaggctgct tctggcccaa cgcagaggtg gacaggttct   180
tcctggcagt gcacgggcac tacttcaggg cctgcccccat ctcaggcagg gccgtgcggg   240
acccgcctgg cagcg                                                    255
```

<210> SEQ ID NO 6
<211> LENGTH: 84
<212> TYPE: PRT
<213> ORGANISM: Macaca cynomolgus

<400> SEQUENCE: 6

```
Ala Leu Leu Gln Glu Leu Cys Leu Thr Gln Phe Gln Val Asp Met Glu
1               5                   10                  15

Ala Val Gly Glu Thr Leu Trp Cys Asp Trp Gly Arg Thr Ile Gly Ser
                20                  25                  30

Tyr Arg Glu Leu Ala Asp Cys Thr Trp His Met Ala Glu Lys Leu Gly
            35                  40                  45

Cys Phe Trp Pro Asn Ala Glu Val Asp Arg Phe Phe Leu Ala Val His
    50                  55                  60
```

```
Gly His Tyr Phe Arg Ala Cys Pro Ile Ser Gly Arg Ala Val Arg Asp
 65                  70                  75                  80

Pro Pro Gly Ser

<210> SEQ ID NO 7
<211> LENGTH: 240
<212> TYPE: DNA
<213> ORGANISM: Marmoset (family Callithricidae)

<400> SEQUENCE: 7
aggaccatca ggagctataa agacctctca gactgcacct ggctcgtggc gcaaaggctg      60
gactgcttct ggcccaacgc ggcggtggac aagttcttcc tgggagtcca ccagcagtac     120
ttcagaaact gccccgtctc cggcagggcc ttgcaggacc cgcccagcag cgtcctctgc     180
cccttcatcg tcgtccccat cctggcgacc ctgctcatga ccgcactggt ggtctggcag     240

<210> SEQ ID NO 8
<211> LENGTH: 80
<212> TYPE: PRT
<213> ORGANISM: Marmoset (family Callithricidae)

<400> SEQUENCE: 8

Arg Thr Ile Arg Ser Tyr Lys Asp Leu Ser Asp Cys Thr Trp Leu Val
  1               5                  10                  15

Ala Gln Arg Leu Asp Cys Phe Trp Pro Asn Ala Ala Val Asp Lys Phe
                 20                  25                  30

Phe Leu Gly Val His Gln Gln Tyr Phe Arg Asn Cys Pro Val Ser Gly
             35                  40                  45

Arg Ala Leu Gln Asp Pro Pro Ser Ser Val Leu Cys Pro Phe Ile Val
         50                  55                  60

Val Pro Ile Leu Ala Thr Leu Leu Met Thr Ala Leu Val Val Trp Gln
 65                  70                  75                  80

<210> SEQ ID NO 9
<211> LENGTH: 1386
<212> TYPE: DNA
<213> ORGANISM: Homo sapien

<400> SEQUENCE: 9
atggagaaaa agtgtaccct gtattttctg gttctcttgc ctttttttat gattcttgtt      60
acagcagaat tagaagagag tcctgaggac tcaattcagt tgggagttac tagaaataaa     120
atcatgacag ctcaatatga atgttaccaa aagattatgc aagaccccat tcaacaagca     180
gaaggcgttt actgcaacag aacctgggat ggatggctct gctggaacga tgttgcagca     240
ggaactgaat caatgcagct ctgccctgat tactttcagg actttgatcc atcagaaaaa     300
gttacaaaga tctgtgacca agatgggaaa tggtttagac atccagcaag caacagaaca     360
tggacaaatt atacccagtg taatgttaac acccacgaga agtgaagac tgcactaaat     420 ttgttttacc tgaccataat tggacacgga ttgtctattg catcactgct tatctcgctt     480
ggcatattct tttatttcaa gagcctaagt tgccaaagga ttaccttaca caaaaatctg     540
ttcttctcat tgttttgtaa ctctgttgta acaatcattc acctcactgc agtggccaac     600
aaccaggcct tagtagccac aaatcctgtt agttgcaaag tgtcccagtt cattcatctt     660
tacctgatgg gctgtaatta cttttggatg ctctgtgaag gcatttacct acacacactc     720
attgtggtgg ccgtgtttgc agagaagcaa catttaatgt ggtattattt tcttggctgg     780
```

-continued

```
ggatttccac tgattcctgc ttgtatacat gccattgcta gaagcttata ttacaatgac    840
aattgctgga tcagttctga tacccatctc ctctacatta tccatggccc aatttgtgct    900
gctttactgg tgaatctttt tttcttgtta aatattgtac gcgttctcat caccaagtta    960
aaagttacac accaagcgga atccaatctg tacatgaaag ctgtgagagc tactcttatc   1020
ttggtgccat tgcttggcat tgaatttgtg ctgattccat ggcgacctga aggaaagatt   1080
gcagaggagg tatatgacta catcatgcac atccttatgc acttccaggg tcttttggtc   1140
tctaccattt tctgcttctt taatggagag gttcaagcaa ttctgagaag aaactggaat   1200
caatacaaaa tccaatttgg aaacagcttt tccaactcag aagctcttcg tagtgcgtct   1260
tacacagtgt caacaatcag tgatggtcca ggttatagtc atgactgtcc tagtgaacac   1320
ttaaatggaa aaagcatcca tgatattgaa atgttctct  taaaaccaga aaatttatat   1380
aattga                                                              1386
```

<210> SEQ ID NO 10
<211> LENGTH: 461
<212> TYPE: PRT
<213> ORGANISM: Homo sapien

<400> SEQUENCE: 10

```
Met Glu Lys Lys Cys Thr Leu Tyr Phe Leu Val Leu Leu Pro Phe Phe
 1               5                  10                  15

Met Ile Leu Val Thr Ala Glu Leu Glu Glu Ser Pro Glu Asp Ser Ile
            20                  25                  30

Gln Leu Gly Val Thr Arg Asn Lys Ile Met Thr Ala Gln Tyr Glu Cys
        35                  40                  45

Tyr Gln Lys Ile Met Gln Asp Pro Ile Gln Gln Ala Glu Gly Val Tyr
    50                  55                  60

Cys Asn Arg Thr Trp Asp Gly Trp Leu Cys Trp Asn Asp Val Ala Ala
65                  70                  75                  80

Gly Thr Glu Ser Met Gln Leu Cys Pro Asp Tyr Phe Gln Asp Phe Asp
                85                  90                  95

Pro Ser Glu Lys Val Thr Lys Ile Cys Asp Gln Asp Gly Asn Trp Phe
            100                 105                 110

Arg His Pro Ala Ser Asn Arg Thr Trp Thr Asn Tyr Thr Gln Cys Asn
        115                 120                 125

Val Asn Thr His Glu Lys Val Lys Thr Ala Leu Asn Leu Phe Tyr Leu
    130                 135                 140

Thr Ile Ile Gly His Gly Leu Ser Ile Ala Ser Leu Leu Ile Ser Leu
145                 150                 155                 160

Gly Ile Phe Phe Tyr Phe Lys Ser Leu Ser Cys Gln Arg Ile Thr Leu
                165                 170                 175

His Lys Asn Leu Phe Phe Ser Phe Val Cys Asn Ser Val Val Thr Ile
            180                 185                 190

Ile His Leu Thr Ala Val Ala Asn Asn Gln Ala Leu Val Ala Thr Asn
        195                 200                 205

Pro Val Ser Cys Lys Val Ser Gln Phe Ile His Leu Tyr Leu Met Gly
    210                 215                 220

Cys Asn Tyr Phe Trp Met Leu Cys Glu Gly Ile Tyr Leu His Thr Leu
225                 230                 235                 240

Ile Val Val Ala Val Phe Ala Glu Lys Gln His Leu Met Trp Tyr Tyr
                245                 250                 255

Phe Leu Gly Trp Gly Phe Pro Leu Ile Pro Ala Cys Ile His Ala Ile
```

|  |  |  |  |  |  |  |  |  |  |  |
|--|--|--|--|--|--|--|--|--|--|--|
|  |  |  | 260 |  |  |  | 265 |  |  | 270 |

Ala Arg Ser Leu Tyr Tyr Asn Asp Asn Cys Trp Ile Ser Ser Asp Thr
            275                        280                        285

His Leu Leu Tyr Ile Ile His Gly Pro Ile Cys Ala Ala Leu Leu Val
  290                        295                        300

Asn Leu Phe Phe Leu Leu Asn Ile Val Arg Val Leu Ile Thr Lys Leu
305                        310                        315                  320

Lys Val Thr His Gln Ala Glu Ser Asn Leu Tyr Met Lys Ala Val Arg
            325                        330                        335

Ala Thr Leu Ile Leu Val Pro Leu Leu Gly Ile Glu Phe Val Leu Ile
          340                        345                        350

Pro Trp Arg Pro Glu Gly Lys Ile Ala Glu Glu Val Tyr Asp Tyr Ile
            355                        360                        365

Met His Ile Leu Met His Phe Gln Gly Leu Leu Val Ser Thr Ile Phe
  370                        375                        380

Cys Phe Phe Asn Gly Glu Val Gln Ala Ile Leu Arg Arg Asn Trp Asn
385                        390                        395                  400

Gln Tyr Lys Ile Gln Phe Gly Asn Ser Phe Ser Asn Ser Glu Ala Leu
            405                        410                        415

Arg Ser Ala Ser Tyr Thr Val Ser Thr Ile Ser Asp Gly Pro Gly Tyr
          420                        425                        430

Ser His Asp Cys Pro Ser Glu His Leu Asn Gly Lys Ser Ile His Asp
            435                        440                        445

Ile Glu Asn Val Leu Leu Lys Pro Glu Asn Leu Tyr Asn
  450                        455                        460

<210> SEQ ID NO 11
<211> LENGTH: 1392
<212> TYPE: DNA
<213> ORGANISM: Rattus Rattus

<400> SEQUENCE: 11

```
atggataaaa agtgtacact ttgttttctg tttctcttgc ttcttaatat ggctctcatc      60
gcagcagagt cggaagaagg cgcgaaccaa acagacttgg gagtcactag gaacaagatc     120
atgacggctc agtatgaatg ttaccaaaag atcatgcagg atcccattca acaaggagaa     180
ggcctttact gcaacagaac ctgggacgga tggctatgct ggaatgacgt tgcagcagga     240
accgagtcaa tgcagtactg ccctgattac tttcaagatt ttgatccttc agagaaggtt     300
acaaagatct gtgaccaaga tggaaactgg ttcagacatc cagatagtaa caggacatgg     360
acaaactaca ccttgtgtaa caacagcacg catgagaaag tgaagacagc actgaatttg     420
ttctacctaa ctataattgg acatggatta tctattgcct ctctgatcat ctcactcatc     480
atatttttt atttcaagag cctaagttgc aacggattac attgcataa aaacctgttc     540
ttttcatttg tttgtaattc gattgtgaca atcattcacc tcacggcagt ggccaataac     600
caggccttag tggccacaaa tcctgtgagc tgcaaggtgt cccagttcat tcatctttac     660
ctgatgggct gtaactactt ttggatgctc tgtgaaggca tttacctgca cactcatt     720
gtggtggctg tgtttgcaga gaagcagcac ttgatgtggt attatttct ggctggggg     780
tttcctctgc ttcctgcctg catccatgcc atcgccagaa gcttgtatta caatgacaac     840
tgctggatca gctcagacac tcatctcctc tacatcatcc atggtcccat tgtgctgct     900
ttactggtaa atctcttttt cctattaaat attgtacgtg ttctcatcac caagttgaaa     960
gttacacacc aagcagaatc caatctctac atgaaagctg taagagccac tctcatcttg    1020
```

-continued

```
gtaccactac ttggcattga atttgtgctt tttccatggc ggcctgaagg aaaggttgct    1080
gaggaggtgt atgactatgt catgcacatt ctcatgcact atcagggtct tttggtgtct    1140
acaattttct gcttctttaa cggagaggtt caagcaattc tgagaagaaa ttggaaccag    1200
tataaaatcc aatttggcaa tggcttttcc cactctgatg ctctccgcag cgcatcctat    1260
acggtgtcaa caatcagcga tgtgcagggg tacagccacg actgccccac tgaacactta    1320
aatggaaaaa gcatccagga tattgaaaat gttgccttaa aaccagaaaa aatgtatgat    1380
ctagtgatgt ga                                                        1392
```

<210> SEQ ID NO 12
<211> LENGTH: 464
<212> TYPE: PRT
<213> ORGANISM: Rattus Rattus

<400> SEQUENCE: 12

```
Met Met Asp Lys Lys Cys Thr Leu Cys Phe Leu Phe Leu Leu Leu Leu
  1               5                  10                  15

Asn Met Ala Leu Ile Ala Ala Glu Ser Glu Glu Gly Ala Asn Gln Thr
             20                  25                  30

Asp Leu Gly Val Thr Arg Asn Lys Ile Met Thr Ala Gln Tyr Glu Cys
         35                  40                  45

Tyr Gln Lys Ile Met Gln Asp Pro Ile Gln Gln Gly Glu Gly Leu Tyr
     50                  55                  60

Cys Asn Arg Thr Trp Asp Gly Trp Leu Cys Trp Asn Asp Val Ala Ala
 65                  70                  75                  80

Gly Thr Glu Ser Met Gln Tyr Cys Pro Asp Tyr Phe Gln Asp Phe Asp
                 85                  90                  95

Pro Ser Glu Lys Val Thr Lys Ile Cys Asp Gln Asp Gly Asn Trp Phe
            100                 105                 110

Arg His Pro Asp Ser Asn Arg Thr Trp Thr Asn Tyr Thr Leu Cys Asn
        115                 120                 125

Asn Ser Thr His Glu Lys Val Lys Thr Ala Leu Asn Leu Phe Tyr Leu
130                 135                 140

Thr Ile Ile Gly His Gly Leu Ser Ile Ala Ser Leu Ile Ile Ser Leu
145                 150                 155                 160

Ile Ile Phe Phe Tyr Phe Lys Ser Leu Ser Cys Gln Arg Ile Thr Leu
                165                 170                 175

His Lys Asn Leu Phe Phe Ser Phe Val Cys Asn Ser Ile Val Thr Ile
            180                 185                 190

Ile His Leu Thr Ala Val Ala Asn Asn Gln Ala Leu Val Ala Thr Asn
        195                 200                 205

Pro Val Ser Cys Lys Val Ser Gln Phe Ile His Leu Tyr Leu Met Gly
    210                 215                 220

Cys Asn Tyr Phe Trp Met Leu Cys Glu Gly Ile Tyr Leu His Thr Leu
225                 230                 235                 240

Ile Val Val Ala Val Phe Ala Glu Lys Gln His Leu Met Trp Tyr Tyr
                245                 250                 255

Phe Leu Gly Trp Gly Phe Pro Leu Leu Pro Ala Cys Ile His Ala Ile
            260                 265                 270

Ala Arg Ser Leu Tyr Tyr Asn Asp Asn Cys Trp Ile Ser Ser Asp Thr
        275                 280                 285

His Leu Leu Tyr Ile Ile His Gly Pro Ile Cys Ala Ala Leu Leu Val
    290                 295                 300
```

| Asn | Leu | Phe | Phe | Leu | Leu | Asn | Ile | Val | Arg | Val | Leu | Ile | Thr | Lys | Leu |
|---|---|---|---|---|---|---|---|---|---|---|---|---|---|---|---|
| 305 | | | | | 310 | | | | | 315 | | | | | 320 |

| Lys | Val | Thr | His | Gln | Ala | Glu | Ser | Asn | Leu | Tyr | Met | Lys | Ala | Val | Arg |
|---|---|---|---|---|---|---|---|---|---|---|---|---|---|---|---|
| | | | | 325 | | | | | 330 | | | | | 335 | |

| Ala | Thr | Leu | Ile | Leu | Val | Pro | Leu | Leu | Gly | Ile | Glu | Phe | Val | Leu | Phe |
|---|---|---|---|---|---|---|---|---|---|---|---|---|---|---|---|
| | | | | 340 | | | | | 345 | | | | | 350 | |

| Pro | Trp | Arg | Pro | Glu | Gly | Lys | Val | Ala | Glu | Val | Tyr | Asp | Tyr | Val |
|---|---|---|---|---|---|---|---|---|---|---|---|---|---|---|
| | | | 355 | | | | | 360 | | | | | 365 | |

| Met | His | Ile | Leu | Met | His | Tyr | Gln | Gly | Leu | Leu | Val | Ser | Thr | Ile | Phe |
|---|---|---|---|---|---|---|---|---|---|---|---|---|---|---|---|
| | 370 | | | | | 375 | | | | | 380 | | | | |

| Cys | Phe | Phe | Asn | Gly | Glu | Val | Gln | Ala | Ile | Leu | Arg | Arg | Asn | Trp | Asn |
|---|---|---|---|---|---|---|---|---|---|---|---|---|---|---|---|
| 385 | | | | | 390 | | | | | 395 | | | | | 400 |

| Gln | Tyr | Lys | Ile | Gln | Phe | Gly | Asn | Gly | Phe | Ser | His | Ser | Asp | Ala | Leu |
|---|---|---|---|---|---|---|---|---|---|---|---|---|---|---|---|
| | | | | 405 | | | | | 410 | | | | | 415 | |

| Arg | Ser | Ala | Ser | Tyr | Thr | Val | Ser | Thr | Ile | Ser | Asp | Val | Gln | Gly | Tyr |
|---|---|---|---|---|---|---|---|---|---|---|---|---|---|---|---|
| | | | | 420 | | | | | 425 | | | | | 430 | |

| Ser | His | Asp | Cys | Pro | Thr | Glu | His | Leu | Asn | Gly | Lys | Ser | Ile | Gln | Asp |
|---|---|---|---|---|---|---|---|---|---|---|---|---|---|---|---|
| | | | 435 | | | | | 440 | | | | | 445 | | |

| Ile | Glu | Asn | Val | Ala | Leu | Lys | Pro | Glu | Lys | Met | Tyr | Asp | Leu | Val | Met |
|---|---|---|---|---|---|---|---|---|---|---|---|---|---|---|---|
| | 450 | | | | | 455 | | | | | 460 | | | | |

<210> SEQ ID NO 13
<211> LENGTH: 1392
<212> TYPE: DNA
<213> ORGANISM: Mus musculus

<400> SEQUENCE: 13

```
atggataaaa agcatatact atgttttctg gttctcttgc ctcttaatat ggctctcatc    60
tcagcagagt cggaagaagg cgtgaaccaa acagacttgg gagtcactag aaacaagatc   120
atgacggctc aatatgaatg ttaccagaag atcatgcagg accccattca acaagcagaa   180
ggccttact gcaataggac ctgggacgga tggctatgct ggaatgacgt tgcagcaggg   240
acggaatcaa tgcagtactg ccctgactat tttcaggatt tgatccttc agagaaggtt   300
acaaagatct gtgaccaaga tggacactgg tttcggcatc cggatagtaa tagaacatgg   360
accaactaca ccctgtgtaa taacagcacg catgagaaag tgaagacagc cctgaatctg   420
ttctacctaa ctataattgg acatggatta tctattgcat ctctgatcat ctctctcatc   480
atatttttt acttcaagag cctaagttgc aacggatca cattgcataa aaacctgttc   540
ttttcattta tttgtaattc aattgtaaca atcatccacc tcacggcagt ggccaataac   600
caggccttag tggccacaaa tcctgtgagc tgcaaagtgt ctcagtttat ccatctctac   660
ctgatgggct gtaactactt ctggatgctc tgtgaaggcg tttacctgca cactcatc    720
gtggtggctg tgtttgcgga gaagcagcac ttgatgtggt attattttct cggctggggg   780
tttcctctgc ttcctgcctg catccacgcc attgccagaa gcttgtatta caacgacaat   840
tgctggatca gctcagacac tcatctcctc tacattatcc atggtccgat tgtgctgct   900
ttgttggtaa atctcttttt cctattaaat attgtacgtg ttctcatcac caagttgaaa   960
gttacacacc aagtgaatc caatctctac atgaaagccg taagagctac tctcatcttg  1020
gtaccactac ttggcattga atttgtgctt tttccgtggc ggcctgaagg aaaggttgca  1080
gaggaggtgt atgactatgt catgcacatt ttgatgcact ttcagggtct tttggtggct  1140
actatttct gcttctttaa tggagaggtt caagcaattc tgagaagaaa ttggaaccag  1200
```

-continued

```
tataaaatcc aatttggaaa tggcttttcc cactctgatg ctctccgcag tgcatcctac    1260
acagtgtcaa caatcagtga catgcaaggg tacagccatg actgccccac tgaacactta    1320
aatggaaaaa gcatccagga tattgaaaat gttgccttaa aatcagaaaa tatgtatgat    1380
ctagtgatgt ga                                                        1392
```

<210> SEQ ID NO 14
<211> LENGTH: 463
<212> TYPE: PRT
<213> ORGANISM: Mus musculus

<400> SEQUENCE: 14

```
Met Asp Lys Lys His Ile Leu Cys Phe Leu Val Leu Leu Pro Leu Asn
1               5                   10                  15

Met Ala Leu Ile Ser Ala Glu Ser Glu Gly Val Asn Gln Thr Asp
            20                  25                  30

Leu Gly Val Thr Arg Asn Lys Ile Met Thr Ala Gln Tyr Glu Cys Tyr
        35                  40                  45

Gln Lys Ile Met Gln Asp Pro Ile Gln Gln Ala Glu Gly Leu Tyr Cys
    50                  55                  60

Asn Arg Thr Trp Asp Gly Trp Leu Cys Trp Asn Asp Val Ala Ala Gly
65                  70                  75                  80

Thr Glu Ser Met Gln Tyr Cys Pro Asp Tyr Phe Gln Asp Phe Asp Pro
                85                  90                  95

Ser Glu Lys Val Thr Lys Ile Cys Asp Gln Asp Gly His Trp Phe Arg
            100                 105                 110

His Pro Asp Ser Asn Arg Thr Trp Thr Asn Tyr Thr Leu Cys Asn Asn
        115                 120                 125

Ser Thr His Glu Lys Val Lys Thr Ala Leu Asn Leu Phe Tyr Leu Thr
    130                 135                 140

Ile Ile Gly His Gly Leu Ser Ile Ala Ser Leu Ile Ile Ser Leu Ile
145                 150                 155                 160

Ile Phe Phe Tyr Phe Lys Ser Leu Ser Cys Gln Arg Ile Thr Leu His
                165                 170                 175

Lys Asn Leu Phe Phe Ser Phe Ile Cys Asn Ser Ile Val Thr Ile Ile
            180                 185                 190

His Leu Thr Ala Val Ala Asn Asn Gln Ala Leu Val Ala Thr Asn Pro
        195                 200                 205

Val Ser Cys Lys Val Ser Gln Phe Ile His Leu Tyr Leu Met Gly Cys
    210                 215                 220

Asn Tyr Phe Trp Met Leu Cys Glu Gly Val Tyr Leu His Thr Leu Ile
225                 230                 235                 240

Val Val Ala Val Phe Ala Glu Lys Gln His Leu Met Trp Tyr Tyr Phe
                245                 250                 255

Leu Gly Trp Gly Phe Pro Leu Leu Pro Ala Cys Ile His Ala Ile Ala
            260                 265                 270

Arg Ser Leu Tyr Tyr Asn Asp Asn Cys Trp Ile Ser Ser Asp Thr His
        275                 280                 285

Leu Leu Tyr Ile Ile His Gly Pro Ile Cys Ala Ala Leu Leu Val Asn
    290                 295                 300

Leu Phe Phe Leu Leu Asn Ile Val Arg Val Leu Ile Thr Lys Leu Lys
305                 310                 315                 320

Val Thr His Gln Val Glu Ser Asn Leu Tyr Met Lys Ala Val Arg Ala
                325                 330                 335
```

```
Thr Leu Ile Leu Val Pro Leu Gly Ile Glu Phe Val Leu Phe Pro
            340                 345                 350

Trp Arg Pro Glu Gly Lys Val Ala Glu Val Tyr Asp Tyr Val Met
        355                 360                 365

His Ile Leu Met His Phe Gln Gly Leu Leu Val Ala Thr Ile Phe Cys
    370                 375                 380

Phe Phe Asn Gly Glu Val Gln Ala Ile Leu Arg Arg Asn Trp Asn Gln
385                 390                 395                 400

Tyr Lys Ile Gln Phe Gly Asn Gly Phe Ser His Ser Asp Ala Leu Arg
                405                 410                 415

Ser Ala Ser Tyr Thr Val Ser Thr Ile Ser Asp Met Gln Gly Tyr Ser
            420                 425                 430

His Asp Cys Pro Thr Glu His Leu Asn Gly Lys Ser Ile Gln Asp Ile
        435                 440                 445

Glu Asn Val Ala Leu Lys Ser Glu Asn Met Tyr Asp Leu Val Met
    450                 455                 460

<210> SEQ ID NO 15
<211> LENGTH: 447
<212> TYPE: DNA
<213> ORGANISM: Homo sapien

<400> SEQUENCE: 15
atggcccggg ccctgtgccg cctcccgcgg cgcggcctct ggctgctcct ggcccatcac      60
ctcttcatga ccactgcctg ccaggaggct aactacggtg ccctcctccg ggagctctgc     120
ctcacccagt tccaggtaga catggaggcc gtcggggaga cgctgtggtg tgactggggc     180
aggaccatca ggagctacag ggagctggcc gactgcacct ggcacatggc ggagaagctg     240
ggctgcttct ggcccaatgc agaggtggac aggttcttcc tggcagtgca tggccgctac     300
ttcaggagct gccccatctc aggcagggcc gtgcgggacc cgcccggcag catcctctac     360
cccttcatcg tggtccccat cacggtgacc ctgctggtga cggcactggt ggtctggcag     420
agcaagcgca ctgagggcat tgtgtag                                         447

<210> SEQ ID NO 16
<211> LENGTH: 148
<212> TYPE: PRT
<213> ORGANISM: Homo sapien

<400> SEQUENCE: 16

Met Ala Arg Ala Leu Cys Arg Leu Pro Arg Arg Gly Leu Trp Leu Leu
1               5                   10                  15

Leu Ala His His Leu Phe Met Thr Thr Ala Cys Gln Glu Ala Asn Tyr
            20                  25                  30

Gly Ala Leu Leu Arg Glu Leu Cys Leu Thr Gln Phe Gln Val Asp Met
        35                  40                  45

Glu Ala Val Gly Glu Thr Leu Trp Cys Asp Trp Gly Arg Thr Ile Arg
    50                  55                  60

Ser Tyr Arg Glu Leu Ala Asp Cys Thr Trp His Met Ala Glu Lys Leu
65                  70                  75                  80

Gly Cys Phe Trp Pro Asn Ala Glu Val Asp Arg Phe Phe Leu Ala Val
                85                  90                  95

His Gly Arg Tyr Phe Arg Ser Cys Pro Ile Ser Gly Arg Ala Val Arg
            100                 105                 110

Asp Pro Pro Gly Ser Ile Leu Tyr Pro Phe Ile Val Val Pro Ile Thr
        115                 120                 125
```

```
Val Thr Leu Leu Val Thr Ala Leu Val Val Trp Gln Ser Lys Arg Thr
    130                 135                 140

Glu Gly Ile Val
145

<210> SEQ ID NO 17
<211> LENGTH: 447
<212> TYPE: DNA
<213> ORGANISM: Rattus rattus

<400> SEQUENCE: 17
atggcccccg gcctgcgggg cctcccgcgg cgcggcctct ggctgctgct ggctcatcat      60
ctcttcatgg tcactgcctg ccgggaccct gactatggta ctctcatcca ggagctgtgt     120
ctcagccgct tcaaagagga catggagacc atagggaaga ctctgtggtg tgactgggga     180
aagaccatag ggagctatgg ggagctcact cactgcacca aactcgtggc aaacaagatt     240
ggctgtttct ggcccaatcc ggaagtggac aagttcttca ttgctgtcca ccaccgctac     300
ttcagcaagt gcccagtctc gggcagggcc ctgcgggacc ctcccaacag catcctctgc     360
cctttcattg tgctccccat tacggtcaca ctgctcatga ctgccctggt ggtctggagg     420
agcaagcgca cagagggcat cgtgtag                                         447

<210> SEQ ID NO 18
<211> LENGTH: 148
<212> TYPE: PRT
<213> ORGANISM: Rattus rattus

<400> SEQUENCE: 18

Met Ala Pro Gly Leu Arg Gly Leu Pro Arg Arg Gly Leu Trp Leu Leu
  1               5                  10                  15

Leu Ala His His Leu Phe Met Val Thr Ala Cys Arg Asp Pro Asp Tyr
                 20                  25                  30

Gly Thr Leu Ile Gln Glu Leu Cys Leu Ser Arg Phe Lys Glu Asp Met
             35                  40                  45

Glu Thr Ile Gly Lys Thr Leu Trp Cys Asp Trp Gly Lys Thr Ile Gly
         50                  55                  60

Ser Tyr Gly Glu Leu Thr His Cys Thr Lys Leu Val Ala Asn Lys Ile
 65                  70                  75                  80

Gly Cys Phe Trp Pro Asn Pro Glu Val Asp Lys Phe Phe Ile Ala Val
                 85                  90                  95

His His Arg Tyr Phe Ser Lys Cys Pro Val Ser Gly Arg Ala Leu Arg
                100                 105                 110

Asp Pro Pro Asn Ser Ile Leu Cys Pro Phe Ile Val Leu Pro Ile Thr
            115                 120                 125

Val Thr Leu Leu Met Thr Ala Leu Val Val Trp Arg Ser Lys Arg Thr
    130                 135                 140

Glu Gly Ile Val
145

<210> SEQ ID NO 19
<211> LENGTH: 447
<212> TYPE: DNA
<213> ORGANISM: Mus musculus

<400> SEQUENCE: 19
atggccccgg gcctgcgggg cctcccgcgg tgcggcctct ggctgctgct ggctcaccat      60
```

```
ctcttcatgg tcactgcctg ccgggaccct gactatggga ctctcatcca ggagctgtgc      120
ctcagccgct tcaaggagaa catggagact attgggaaga cgctatggtg tgactgggga      180
aagaccatac agagctatgg ggagctcact tactgcacca gcacgtggc gcacacgatt       240 ggctgtttct ggcccaatcc ggaagtggac agattcttca tcgctgtcca ccatcgatac      300
ttcagcaagt gccccatctc gggcagggcc ctgcgggacc ctcccaacag catcctctgc      360
cctttcattg cgctccccat tacggtcacg ctgctcatga ctgcactggt ggtctggagg      420
agcaagcgca cagagggcat cgtgtag                                         447
```

```
<210> SEQ ID NO 20
<211> LENGTH: 148
<212> TYPE: PRT
<213> ORGANISM: Mus musculus

<400> SEQUENCE: 20

Met Ala Pro Gly Leu Arg Gly Leu Pro Arg Cys Gly Leu Trp Leu Leu
 1               5                   10                  15

Leu Ala His His Leu Phe Met Val Thr Ala Cys Arg Asp Pro Asp Tyr
             20                  25                  30

Gly Thr Leu Ile Gln Glu Leu Cys Leu Ser Arg Phe Lys Glu Asn Met
         35                  40                  45

Glu Thr Ile Gly Lys Thr Leu Trp Cys Asp Trp Gly Lys Thr Ile Gln
     50                  55                  60

Ser Tyr Gly Glu Leu Thr Tyr Cys Thr Lys His Val Ala His Thr Ile
 65                  70                  75                  80

Gly Cys Phe Trp Pro Asn Pro Glu Val Asp Arg Phe Phe Ile Ala Val
                 85                  90                  95

His His Arg Tyr Phe Ser Lys Cys Pro Ile Ser Gly Arg Ala Leu Arg
            100                 105                 110

Asp Pro Pro Asn Ser Ile Leu Cys Pro Phe Ile Ala Leu Pro Ile Thr
        115                 120                 125

Val Thr Leu Leu Met Thr Ala Leu Val Val Trp Arg Ser Lys Arg Thr
    130                 135                 140

Glu Gly Ile Val
145
```

```
<210> SEQ ID NO 21
<211> LENGTH: 255
<212> TYPE: DNA
<213> ORGANISM: Macaca cynomolgus

<400> SEQUENCE: 21
gtgccctcct ccaggagctc tgcctcaccc agttccaggt agacatggag gccgtcgggg      60
agacgctgtg gtgtgactgg ggcaggacca tcgggagcta cagggagctg ccgactgca       120 cctgtcacat ggcggagaag ctaggctgct tctggcccaa cgcagaggtg acaggttct       180 tcctggcagt gcacgggcac tacttcaggg cctgccccat ctcaggcagg gccgtgcggg      240
acccgcctgg cagcg                                                      255
```

```
<210> SEQ ID NO 22
<211> LENGTH: 84
<212> TYPE: PRT
<213> ORGANISM: Macaca cynomolgus

<400> SEQUENCE: 22

Ala Leu Leu Gln Glu Leu Cys Leu Thr Gln Phe Gln Val Asp Met Glu
```

-continued

```
 1               5                  10                  15

Ala Val Gly Glu Thr Leu Trp Cys Asp Trp Gly Arg Thr Ile Gly Ser
            20                  25                  30

Tyr Arg Glu Leu Ala Asp Cys Thr Cys His Met Ala Glu Lys Leu Gly
        35                  40                  45

Cys Phe Trp Pro Asn Ala Glu Val Asp Arg Phe Phe Leu Ala Val His
    50                  55                  60

Gly His Tyr Phe Arg Ala Cys Pro Ile Ser Gly Arg Ala Val Arg Asp
65                  70                  75                  80

Pro Pro Gly Ser

<210> SEQ ID NO 23
<211> LENGTH: 240
<212> TYPE: DNA
<213> ORGANISM: Porcine

<400> SEQUENCE: 23
aggaccatca ggagctataa agacctctca gactgcacca ggctcgtggc gcaaaggctg     60
gactgcttct ggcccaacgc ggcggtggac aagttcttcc tgggagtcca ccagcagtac    120
ttcagaaact gccccgtctc cggcagggcc ttgcaggacc cgcccagcag cgtcctctgc    180
cccttcatcg tcgtccccat cctggcgacc ctgctcatga ccgcactggt ggtctggcag    240

<210> SEQ ID NO 24
<211> LENGTH: 80
<212> TYPE: PRT
<213> ORGANISM: Porcine

<400> SEQUENCE: 24

Arg Thr Ile Arg Ser Tyr Lys Asp Leu Ser Asp Cys Thr Arg Leu Val
 1               5                  10                  15

Ala Gln Arg Leu Asp Cys Phe Trp Pro Asn Ala Ala Val Asp Lys Phe
            20                  25                  30

Phe Leu Gly Val His Gln Gln Tyr Phe Arg Asn Cys Pro Val Ser Gly
        35                  40                  45

Arg Ala Leu Gln Asp Pro Pro Ser Ser Val Leu Cys Pro Phe Ile Val
    50                  55                  60

Val Pro Ile Leu Ala Thr Leu Leu Met Thr Ala Leu Val Val Trp Gln
65                  70                  75                  80

<210> SEQ ID NO 25
<211> LENGTH: 20
<212> TYPE: DNA
<213> ORGANISM: Artificial Sequence
<220> FEATURE:
<223> OTHER INFORMATION: oligonucleotide

<400> SEQUENCE: 25
ctgccaggag gctaactacg                                                 20

<210> SEQ ID NO 26
<211> LENGTH: 20
<212> TYPE: DNA
<213> ORGANISM: Artificial Sequence
<220> FEATURE:
<223> OTHER INFORMATION: oligonucleotide

<400> SEQUENCE: 26
cacgatgaag ggtagagga                                                  20
```

<210> SEQ ID NO 27
<211> LENGTH: 33
<212> TYPE: DNA
<213> ORGANISM: Artificial Sequence
<220> FEATURE:
<223> OTHER INFORMATION: oligonucleotide

<400> SEQUENCE: 27
ctcactcact gcacctggct cgtggcaaac aag         33

<210> SEQ ID NO 28
<211> LENGTH: 33
<212> TYPE: DNA
<213> ORGANISM: Artificial Sequence
<220> FEATURE:
<223> OTHER INFORMATION: oligonucleotide

<400> SEQUENCE: 28
cttgtttgcc acgagccagg tgcagtgagt gag         33

<210> SEQ ID NO 29
<211> LENGTH: 33
<212> TYPE: DNA
<213> ORGANISM: Artificial Sequence
<220> FEATURE:
<223> OTHER INFORMATION: oligonucleotide

<400> SEQUENCE: 29
tagctagcgc caccatggat aaaaagcata tac         33

<210> SEQ ID NO 30
<211> LENGTH: 28
<212> TYPE: DNA
<213> ORGANISM: Artificial Sequence
<220> FEATURE:
<223> OTHER INFORMATION: oligonucleotide

<400> SEQUENCE: 30
cgggatcctg gctatccaat cttttggc         28

<210> SEQ ID NO 31
<211> LENGTH: 30
<212> TYPE: DNA
<213> ORGANISM: Artificial Sequence
<220> FEATURE:
<223> OTHER INFORMATION: oligonucleotide

<400> SEQUENCE: 31
atgcggccgc gtggggctct gcttgccatg         30

<210> SEQ ID NO 32
<211> LENGTH: 29
<212> TYPE: DNA
<213> ORGANISM: Artificial Sequence
<220> FEATURE:
<223> OTHER INFORMATION: oligonucleotide

<400> SEQUENCE: 32
cgggatccct catcacctgg gatacctac         29

<210> SEQ ID NO 33
<211> LENGTH: 34
<212> TYPE: DNA
<213> ORGANISM: Artificial Sequence
<220> FEATURE:
<223> OTHER INFORMATION: oligonucleotide

```
<400> SEQUENCE: 33
gctcacttac tgcacctggc acgtggcgca cacg                              34

<210> SEQ ID NO 34
<211> LENGTH: 34
<212> TYPE: DNA
<213> ORGANISM: Artificial Sequence
<220> FEATURE:
<223> OTHER INFORMATION: oligonucleotide

<400> SEQUENCE: 34
cgtgtgcgcc acgtgccagg tgcagtaagt gagc                              34
```

What is claimed:

1. A purified nucleic acid molecule encoding a mammalian receptor-activity modifying protein 1 which comprises a nucleotide sequence selected from the group consisting of SEQ ID NO: 1 and 3.

2. An expression vector for expressing a mammalian receptor-activity modifying protein 1 in a recombinant isolated host cell wherein said expression vector comprises a nucleic acid molecule of claim 1.

3. A isolated host cell which expresses a recombinant mammalian receptor-activity modifying protein 1 wherein said host cell contains the expression vector of claim 2.

4. A process for expressing a mammalian receptor-activity modifying protein 1 in a recombinant isolated host cell, comprising:
   (a) transfecting the expression vector of claim 2 into a suitable host cell; and,
   (b) culturing the host cells of step (a) under conditions which allow expression of said protein from said expression vector.

5. A purified mammalian receptor-activity modifying protein 1 comprising an amino acid sequence selected from the group consisting of SEQ ID NOs: 2 and 4.

6. A membrane preparation comprising the mammalian receptor-activity modifying protein 1 purified from the recombinant host cell of claim 3.

7. The membrane preparation of claim 6 which further comprises a mammalian calcitonin-receptor-like receptor protein, such that a receptor-activity modifying protein 1-calcitonin-receptor-like receptor protein complex, in the presence of Compound 1, Compound 2, and BIBN4096BS, exhibits $IC_{50}$ values comparable to that of the human complex.

8. The membrane preparation of claim 7 wherein the calcitonin-receptor-like receptor protein is selected from the group consisting of SEQ ID NOs: 10, 12 and 14.

* * * * *